(12) United States Patent
Osman

(10) Patent No.: US 10,440,240 B2
(45) Date of Patent: Oct. 8, 2019

(54) SYSTEMS AND METHODS FOR REDUCING AN EFFECT OF OCCLUSION OF A TRACKER BY PEOPLE

(71) Applicant: Sony Interactive Entertainment Inc., Tokyo (JP)

(72) Inventor: Steven Osman, San Francisco, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 15/699,844

(22) Filed: Sep. 8, 2017

(65) Prior Publication Data

US 2018/0097975 A1  Apr. 5, 2018

Related U.S. Application Data

(60) Provisional application No. 62/402,996, filed on Sep. 30, 2016.

(51) Int. Cl.
| | | |
|---|---|---|
| *A63F 9/00* | (2006.01) |
| *H04N 5/222* | (2006.01) |
| *H04N 13/106* | (2018.01) |
| *B25J 9/16* | (2006.01) |
| *A63F 13/211* | (2014.01) |
| *A63F 13/213* | (2014.01) |
| *A63F 13/533* | (2014.01) |
| *A63F 13/54* | (2014.01) |
| *A61B 34/20* | (2016.01) |
| *G01S 5/16* | (2006.01) |
| *G03B 9/60* | (2006.01) |

(52) U.S. Cl.
CPC ......... *H04N 5/2226* (2013.01); *A63F 13/211* (2014.09); *A63F 13/213* (2014.09); *A63F 13/533* (2014.09); *A63F 13/54* (2014.09); *B25J 9/1602* (2013.01); *B25J 9/1697* (2013.01); *H04N 13/106* (2018.05); *A61B 2034/2057* (2016.02); *A63F 2300/8082* (2013.01); *G01S 5/16* (2013.01); *G03B 9/60* (2013.01)

(58) Field of Classification Search
None
See application file for complete search history.

(56) References Cited

U.S. PATENT DOCUMENTS

| | | | |
|---|---|---|---|
| 3,893,134 A | 7/1975 | Brüuning | 354/30 |
| 8,744,260 B2 | 6/2014 | Shida | 396/260 |

(Continued)

OTHER PUBLICATIONS

Mansurov, Understanding ISO, Shutter Speed and Aperture-A Beginner's Guidepp. 1/41-6/41, https://photographylife.com/iso-shutter-speed-and-aperture-for-beginners.

(Continued)

*Primary Examiner* — Seng Heng Lim
(74) *Attorney, Agent, or Firm* — Penilla IP, APC

(57) ABSTRACT

Systems and methods for reducing an effect of occlusion of a tracker by people are described. When a user is playing a video game using a head-mounted display, a field-of-view for tracking the user is obstructed by a spectator. The video game cannot be displayed at a normal frame rate to the user as a result of the obstruction. The systems and methods described herein determine and identify a source of the obstruction, and implement operations to remove the obstruction.

24 Claims, 24 Drawing Sheets

(56) References Cited

U.S. PATENT DOCUMENTS

| | | | | |
|---|---|---|---|---|
| 2011/0175810 A1* | 7/2011 | Markovic | ............... | G06F 3/011 345/158 |
| 2013/0335573 A1* | 12/2013 | Forutanpour | ........... | G06F 3/011 348/158 |
| 2014/0306994 A1 | 10/2014 | Brown et al. | .................. | 345/633 |
| 2015/0094142 A1 | 4/2015 | Stafford | ......................... | 463/31 |
| 2015/0317832 A1* | 11/2015 | Ebstyne | .................. | G06F 3/011 345/633 |
| 2016/0266471 A1 | 9/2016 | Prados | ..................... | G03B 9/60 |
| 2017/0274277 A1* | 9/2017 | Vandonkelaar | ....... | A63F 13/211 |

OTHER PUBLICATIONS

Unknown, "Focusing Basics / Aperture and Depth of Field", pp. 1/9-5/9, http://www.exposureguide.com/focusing-basics.htm.

Unknown, "Camera Exposure: Aperture, ISO & Shutter Speed", pp. 1/9-9/9, http://www.cambridgeincolour.com/tutorials/camera-exposure.htm.

Int'l App. No. PCT/US2017/053272, International Search Report, dated Dec. 11, 2017.

* cited by examiner (Outside-in Tracking)

(Outside-in Tracking)

(Inside-Out Tracking)

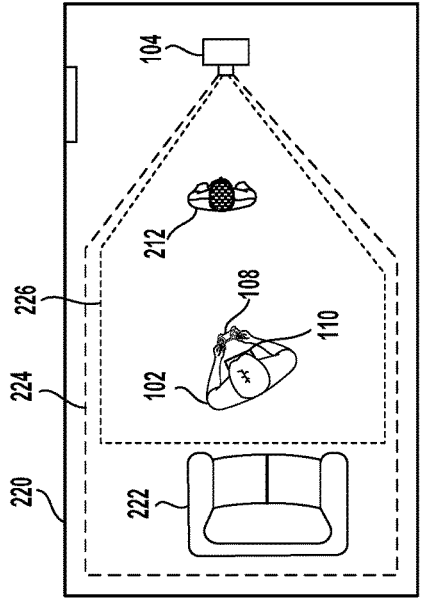
FIG. 2C (Obstruction)
(Outside-in Tracking)
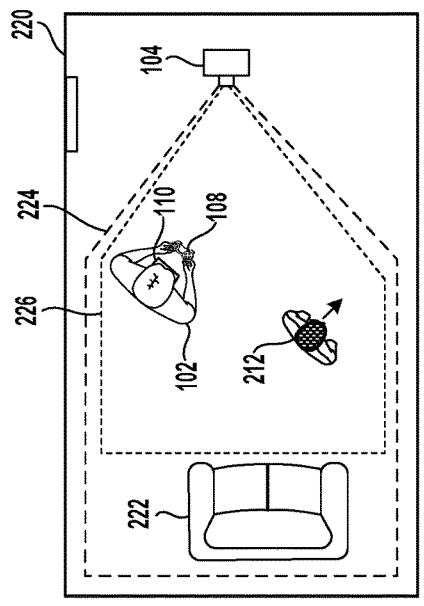
FIG. 2B (No Obstruction)
(Outside-in Tracking)
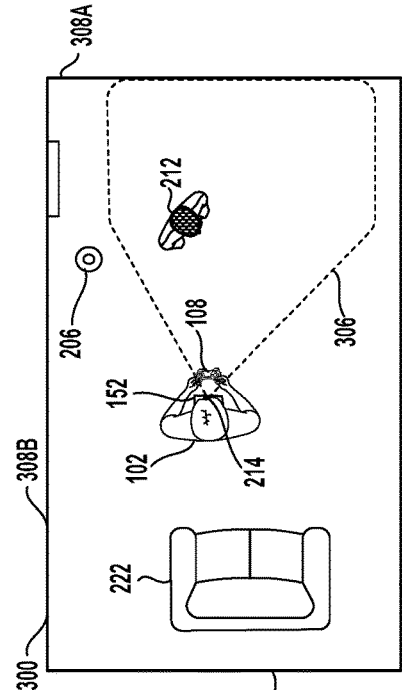
FIG. 3B (Obstruction)
(Inside-Out Tracking)
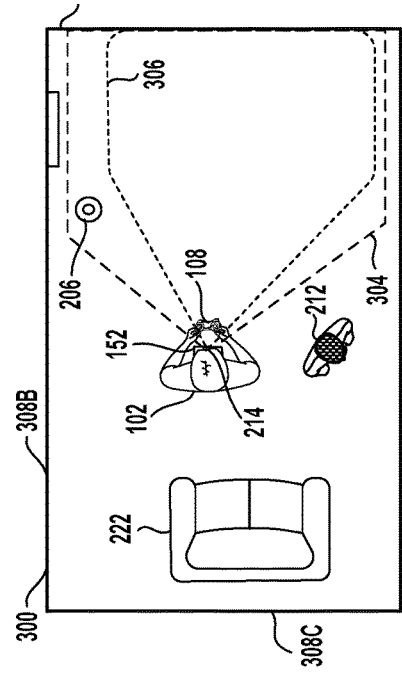
FIG. 3A (No Obstruction)
(Inside-Out Tracking)

FIG. 4B (Camera View)

(Position/Orientation Tracking)

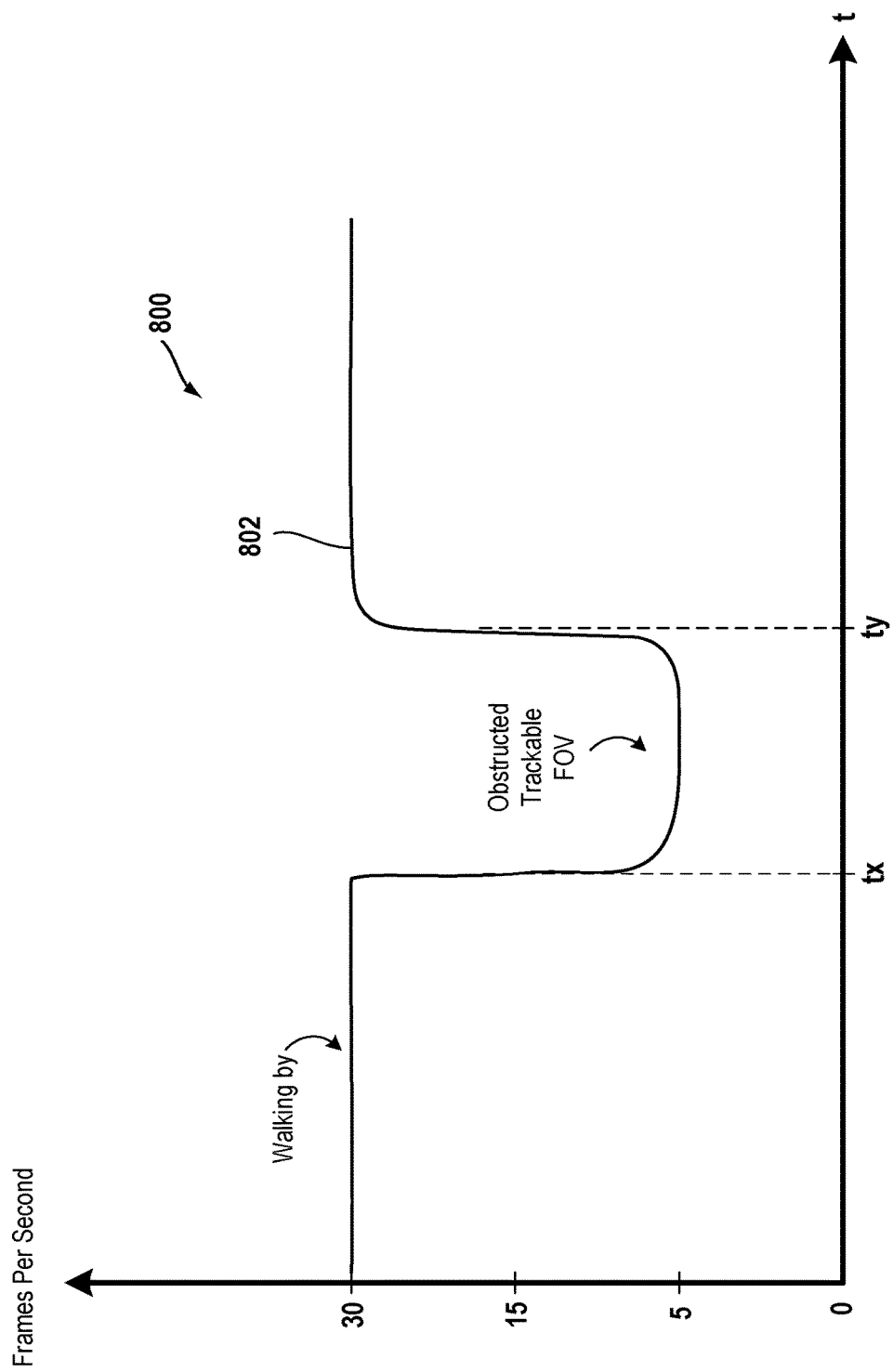

SYSTEMS AND METHODS FOR REDUCING AN EFFECT OF OCCLUSION OF A TRACKER BY PEOPLE

This application claims priority, under 35 U.S.C. § 119(e), to US Provisional Patent Application No. 62/402,996, entitled "Systems and Methods for Reducing an Effect of Occlusion of a Tracker by People," filed on Sep. 30, 2016, which is herein incorporated by reference.

FIELD

The present disclosure relates to systems and methods for reducing an effect of occlusion of a tracker by people.

BACKGROUND

Typically, a head-mounted display (HMD) is a portable device worn around the head, such that a display situated a short distance from the eyes provides images for user interaction. Sometimes HMDs provide a mixed real-life and virtual life environments, where the user is able to see images created by a computing device, as well as some real-live images. Other times HMDs provide immersive experiences that block the outside world to the user, while providing a virtual world on the HMD display. However, gaming using HMD devices still need much improvement.

It is within this context that embodiments described in the present disclosure arise.

SUMMARY

In some embodiments, a method for identifying an obstruction to a trackable field-of-view (FOV) of a tracker is described. The method includes executing a video game for display on a head-mounted display (HMD). The HMD is worn by a user. The execution of the video game is changed based on a position and orientation of the head-mounted display when tracked by the tracker. The method further includes determining whether the trackable FOV is obstructed by a spectator during the execution of the video game. The obstruction by the spectator impedes a determination of the position and orientation. The method includes identifying the spectator upon determining that the spectator is obstructing the trackable FOV and generating a notification to be output via the head-mounted display to remove the obstruction to the trackable FOV.

In various embodiments, a method for identifying a spectator to a user during play of a video game on a head-mounted display is described. The method includes determining whether a spectator is within a trackable FOV of a tracker. The operation of determining whether the spectator is within the trackable FOV is performed when a video game code is executed to display the video game on the head-mounted display. The head-mounted display is worn by the user during the play of the video game. The method further includes determining whether the spectator is identifiable upon determining that the spectator is within the trackable FOV, determining whether the spectator is obstructing the trackable FOV in response to determining that the spectator is not identifiable when in the trackable FOV, and determining whether the spectator is obstructing the trackable FOV upon determining that the spectator is obstructing the trackable FOV. The method includes notifying the user that the spectator is obstructing the trackable FOV in response to determining that the spectator is obstructing the trackable FOV.

In several embodiments, a system for identifying an obstruction to a trackable field-of-view (FOV) of a tracker is described. The system includes a head-mounted display configured to be worn by a user and a processor coupled to the head-mounted display that is worn by a user during a play of a video game. The processor is configured to execute a video game code for display of the video game on the head-mounted display. The execution of the video game code is changed based on a position and orientation of the head-mounted display when tracked by the tracker. The processor is further configured to determine whether the trackable FOV is obstructed by a spectator during the execution of the video game. The obstruction by the spectator impedes a determination of the position and orientation. The processor is further configured to identify the spectator upon determining that the spectator is obstructing the trackable FOV and generate a notification to be output via the head-mounted display to remove the obstruction to the trackable FOV.

Some advantages of the herein described systems and methods for reducing an effect of occlusion of a tracker by people include determining a cause of a slowdown in display of a video game on a head-mounted display (HMD). For example, an exposure of a camera that is viewing a real-world environment in which a user is wearing the HMD to play game is modified to determine whether a spectator is blocking a trackable field-of-view (FOV) of the camera and to identify the spectator. The blocking creates a reduction, e.g., a freeze, etc., in a frame rate with which images are displayed on the HMD. As such, by determining that the spectator is blocking the trackable FOV and identifying the spectator, the cause of the slowdown in the display of images of the video game on the HMD is determined.

Other advantages include removing the cause of the slowdown in the display of images on the HMD. When the user is notified of the identity of the spectator, the HMD issues a vocal request to a real-world environment in which the user is playing the video game and the vocal request identifies the spectator and further requests the spectator to unblock the trackable FOV. The spectator, upon receiving the vocal request, moves to not obstruct the trackable FOV to further allow the user to play the video game on the HMD. Hence, the cause of the slowdown is removed.

Yet other advantages include applying the cause to award the user with extra credits to compensate for the slowdown in the display of the video game. For example, the user is awarded with extra time to play the video game or with extra credits in the video game to reduce an effect of the obstruction of the trackable FOV on the game play by the user.

BRIEF DESCRIPTION OF THE DRAWINGS

FIG. 2B is a top-view of an embodiment of an environment in which the user is located and out-side in tracking is performed by a camera.

FIG. 2C is a top-view of an environment in which a spectator is obstructing a head-mounted display (HMD) and a hand-held controller from a view of the camera.

FIG. 3A is a top-view of an embodiment of an environment in which the user is located and inside-out tracking is performed by an HMD.

FIG. 3B is a top-view of an environment in which the spectator is obstructing a trackable FOV of an HMD.

FIG. 4B is a diagram of an embodiment of a view of an environment from a lens of a camera.

FIG. 8A is an embodiment of a graph to illustrate a change in a frame rate at which consecutive images of the video game are displayed on the one or more display screens of an tracker.

DETAILED DESCRIPTION OF THE EMBODIMENTS

Systems and methods for reducing an effect of occlusion of a tracker by people include determining a cause of a slowdown in display of a video game on a head-mounted display (HMD) are described. In some embodiments, the systems and methods use face detection and stereo or three-dimensional reconstruction to identify other people walking around in a room in which a user wearing the HMD is located. The systems and methods alert the user that his/her tracking is of poor quality because a spectator is detected walking in front of a camera. The camera is used to track movement of the user by tracking movement of the HMD and/or a hand-held controller carried by the user. In various embodiments, to identify the spectator, an exposure of the camera is changed. In some embodiments, the exposure of the camera is modified when a quality of tracking the user becomes worse.

Figure 1A:
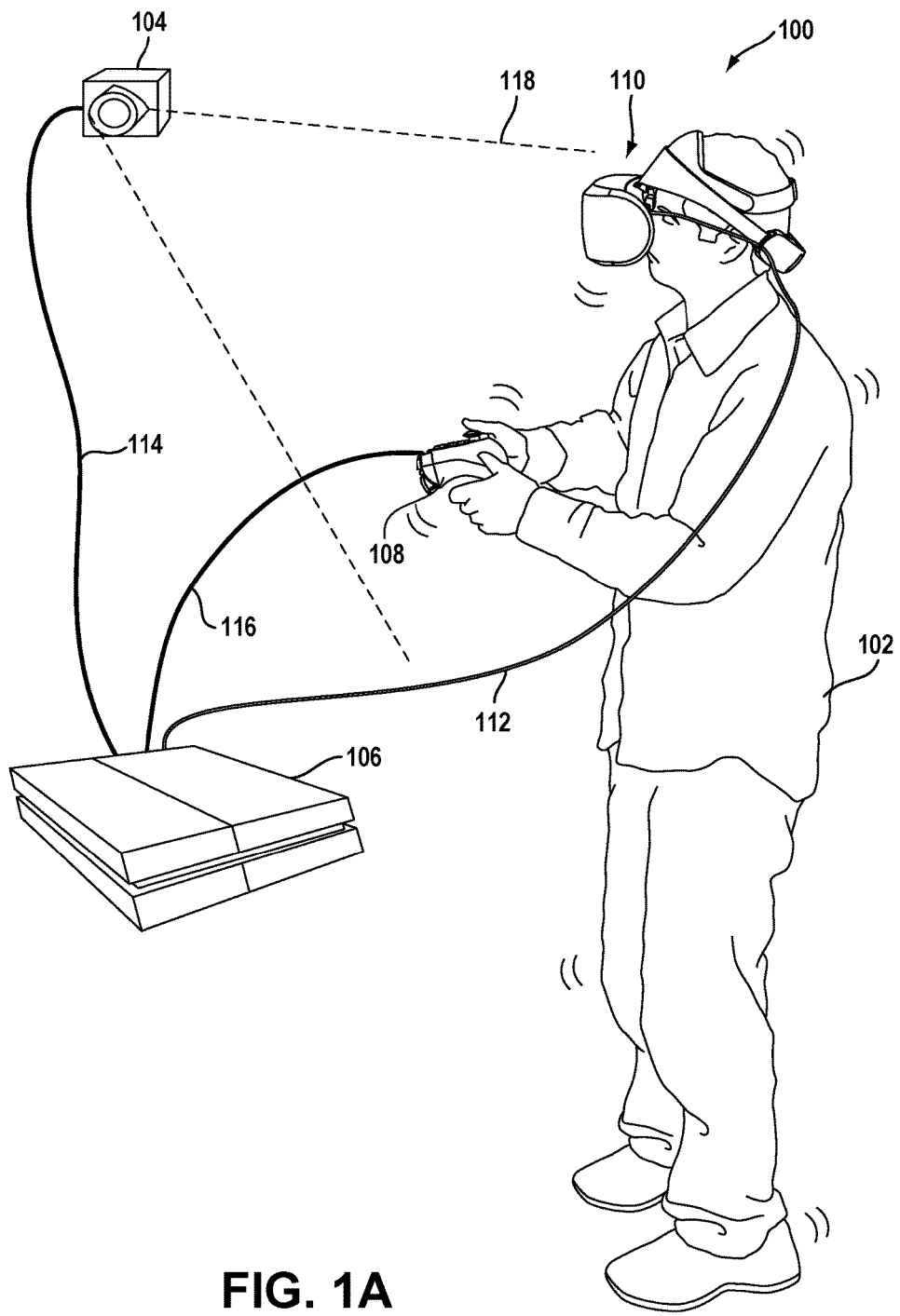
FIG. 1A is a diagram of an embodiment of a system to illustrate outside-in tracking of a user.

FIG. 1A is a diagram of an embodiment of a system 100 to illustrate outside-in tracking of a user 102, who is sometimes referred to herein as a player. The system 100 includes a camera 104, a game console 106, a hand-held controller 108, and an HMD 110. Examples of the camera 104 include a depth camera, a camcorder, a video camera, a digital camera, or any other optical instrument capable of recording or capturing images, etc. Examples of the game console 106 include an electronic, digital, or computer device that outputs a video signal or image data to display a video game. Examples of the hand-held controller 108 include an input device that is used by the user 102 to interact with the video game. The video game is displayed on one or more display screens of the HMD 110, which is worn by the user 102 on his/her head and covers eyes of the user 102. Examples of the HMD 110 include a display device that displays virtual reality (VR) images or augmented reality (AR) images. The game console 106 is coupled to the HMD 108 via a communication medium 112. Examples of a communication medium, as described herein, include a wired medium, e.g., a cable, one or more electrical conductors, etc., or a wireless medium, e.g., Wi-Fi™, Bluetooth™, radio frequency (RF), etc. Moreover, the camera 104 is coupled to the game console 106 via a communication medium 114. Also, the hand-held controller 108 is coupled to the game console 106 via a communication medium 116.

The game console 106 executes a game code to generate image data of the video game. The image data is transferred via the communication medium 112 to the HMD 110 for rendering images on the one or more display screens of the HMD 102. The user 102 views the images that are displayed on the HMD 102, and uses the hand-held controller 108 to provide input to the video game. Moreover, the user 102 moves during the play of the video game from one location to another in a real-world environment, e.g., a room, a floor of a building, office, a house, an apartment, etc. The user 102 also moves the hand-held controller 108 and/or selects one or more buttons of the hand-held controller 108. When the one or more buttons of the hand-held controller 108 are selected, one or more input signals are generated by the hand-held controller 108.

The camera 104 captures images of any real-world objects, e.g., the HMD 110 and the hand-held controller 108, etc., which are within a field-of-view (FOV) 118 of the camera 104. For example, the camera 104 captures images of light emitted by light sources, e.g., light emitting diodes (LEDs), e.g., or other markers, e.g., reflective tape, etc., on the HMD 110 and on the hand-held controller 108. The FOV 118 includes all real-world objects that the camera 104 is able to capture images of. In some embodiments, the camera 104, in addition to capturing the images of the HMD 110 and the hand-held controller 108, captures images of the user 102. The camera 104 sends image data for the images via the communication medium 114 to the game console 106. A processor of the game console 106 processes the image data received from the camera 104 to determine a position and an orientation of the HMD 102 and the controller 108. Examples of a processor include an application specific integrated circuit (ASIC), a programmable logic device (PLD), a central processing unit (CPU), a microprocessor, a multi-core processor, or any other processing unit, etc.

The input signals are sent from the hand-held controller 108 via the communication medium 116 to the game console 106. The processor of the game console 106 determines a next game state in the game code of the video game from the input signals, the position and orientation of the HMD 110, and/or the position and orientation of the hand-held controller 108. The game state includes a position and orientation of an image of the video game to be displayed on the HMD 110 and a scene within the video game. For example, as the user 102 moves his/her head from left to right or right to left to move the HMD 110, the scene of the video game includes virtual objects that were not visible in the scene before the movement. The scene is formed by virtual objects, colors, textures, intensity levels, locations of the virtual objects, a width, a length, a dimension, a background, a number of the virtual objects, a size of the virtual objects, etc. Examples of the virtual objects include a car, an avatar, a house, a dog, a sword, a knife, a gun, or any other object that does not exist in the real world, etc.

In some embodiments, instead of the hand-held controller 108 of the shape shown in FIG. 1A, hand-held controllers of other shapes, e.g., sword-shaped hand-held controller, a gun-shaped hand-held controller, a stick-shaped hand-held controller, a MOVE™ hand-held controller, etc., is used by the user 102 to play the video game.

In various embodiments, instead of the game console 106, any other type of computing device, which is further described below, is used.

Figure 1B:
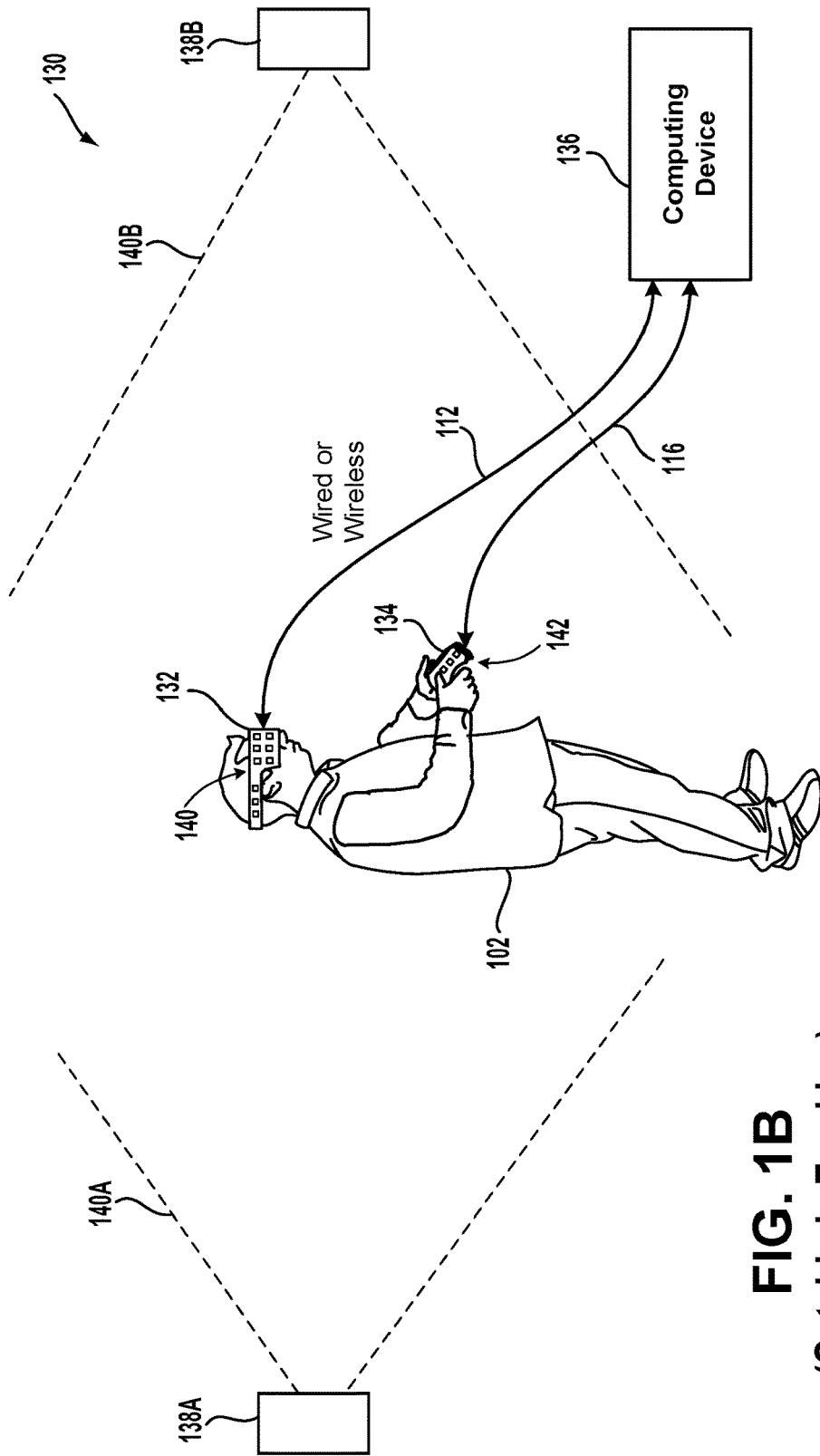
FIG. 1B is a diagram of an embodiment of a system to illustrate outside-in tracking of the user.

FIG. 1B is a diagram of an embodiment of a system 130 to illustrate outside-in tracking of the user 102. The system 130 includes an HMD 132, a hand-held controller 134, a computing device 136, and projectors 138A and 138B. Examples of the computing device 136 include a laptop computer, a desktop computer, a game console, a smartphone, etc. Examples of a projector, as used herein, includes a projector having a Micro-Electro-Mechanical Systems (MEMS) mirror and a laser source, a projector having a laser source, a projector having an infrared light source, or a projector that projects light to scan a volume in the real-world environment, etc. The HMD 132 has photosensors 140, which are shown as small blocks within the HMD 132. The hand-held controller 134 also has photosensors 142, which are shown as small blocks within the hand-held controller 134. The HMD 132 is connected to the computing device 136 via the communication medium 112 and the hand-held controller 134 is connected to the computing device 136 via the communication medium 116.

The projectors 138A and 138B emit light to scan the volume within the environment. For example, the projector 138A has an FOV 140A, which is a volume that is scanned by the light that is emitted by the projector 138A. As another example, the projector 138B has an FOV 140B, which is a volume that is scanned by the light that is emitted by the projector 138B. The volume within the environment that is scanned by the projectors 138A and 138B is a combination of the volume that is scanned by the light emitted by the projector 138A and the volume that is scanned by the light emitted by the projector 138B.

The photosensors 132 sense the light that is emitted by the projectors 138A and 138B to generate electrical signals and send the electrical signals via the communication medium 112 to the computing device 136. Similarly, the photosensors 142 sense the light that is emitted by the projectors 138A and 138B to generate electrical signals and send the electrical signals via the communication medium 116 to the computing device 136. A processor of the computing device 136 calculates a position and orientation of the HMD 132 from the electrical signals received via the communication medium 112 and calculates a position and orientation of the hand-held controller 134 from the electrical signals received via the communication medium 116.

In some embodiments, instead of two projectors 138A and 138B, any other number, e.g., one, three, four, etc., number of projectors is used in the environment in which the user 102 is playing the video game.

In various embodiments, instead of the hand-held controller 134, the hand-held controller controller 108 (FIG. 1A) is used, and the camera 104 (FIG. 1A) is also used to determine the position and orientation of the hand-held controller 108 and the HMD 132.

In some embodiments, instead of or in addition to the projectors 138A and 138B, ultrasonic sound emitters are used. Moreover, the HMD 132 includes ultrasonic sensors instead of or in addition to the photosensors and the hand-held controller 134 includes ultrasonic sensors instead of or in addition to the photosensors.

Figure 1C:
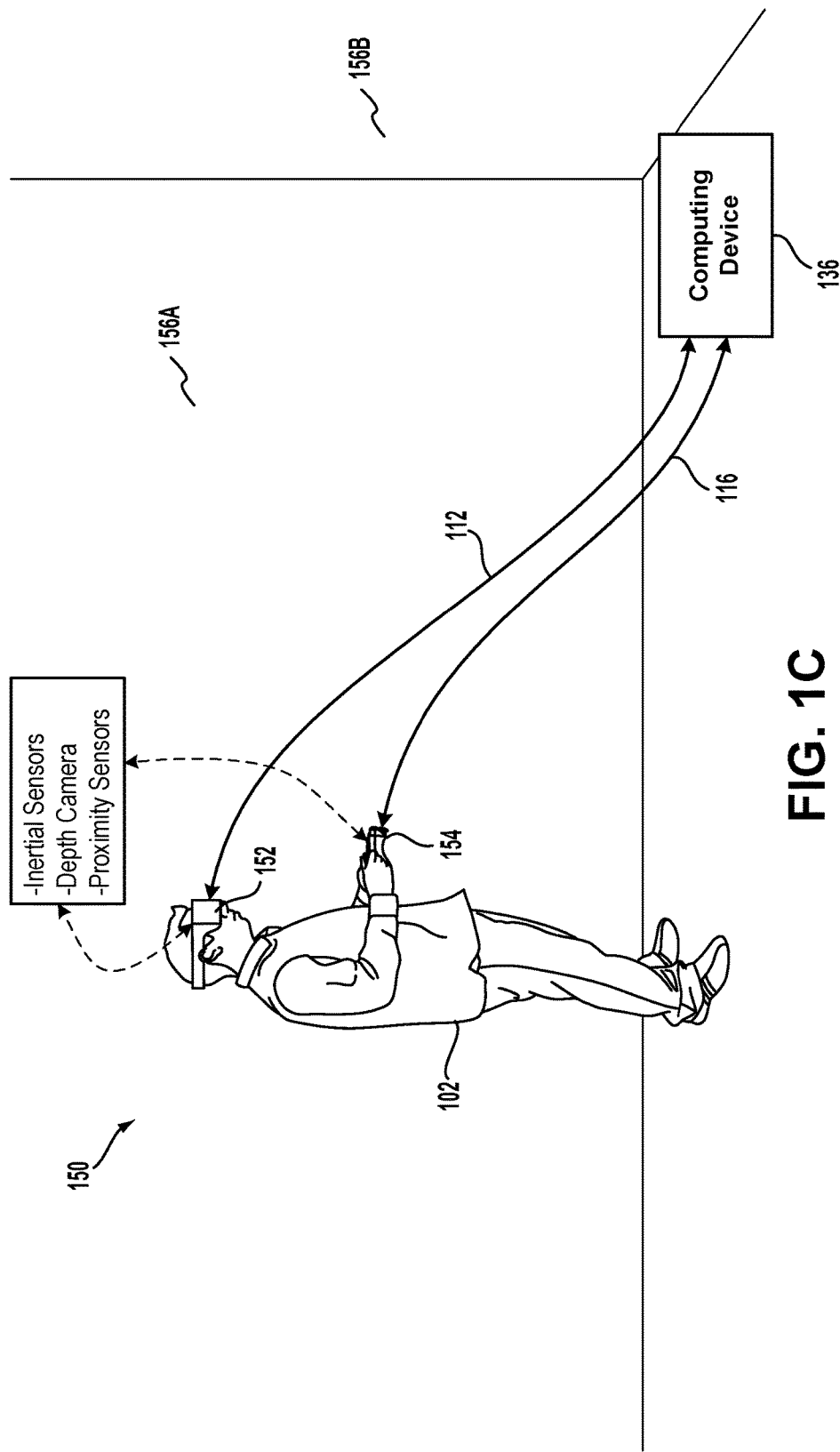
FIG. 1C is a diagram of an embodiment of a system to illustrate inside-out tracking of the user.

FIG. 1C is a diagram of an embodiment of a system 150 to illustrate inside-out tracking of the user 102. The system 150 includes an HMD 152, a hand-held controller 154, and the computing device 136. The HMD 152 includes one or more position and orientation measurement devices, e.g., inertial sensors, one or more depth cameras, and/or proximity sensors, etc., for determining a position and orientation of the HMD 152. For example, the HMD 152 has one or more depth cameras and each depth camera has a lens that faces the real-world environment to capture images of real-world objects, e.g., walls, table, chair, lamp, etc., in the real-world environment and the hand-held controller 154. An example of a proximity sensor is a sensor that emits an electromagnetic radiation, e.g., infrared radiation, etc., and senses changes in a return signal, which is a signal returned from the real-world environment, e.g., walls 156A and 156B of a room, another person in the room, a real-world object in the room, etc. Examples of the inertial sensors include magnetometers, accelerometers, and gyroscopes. Similarly, the hand-held controller 154 includes one or more position and orientation measurement devices for determining a position and orientation of the hand-held controller 154. The HMD 152 is connected to the computing device 136 via the connection medium 112 and the hand-held controller 154 is connected to the computing device 136 via the connection medium 116.

The one or more position and orientation measurement devices of the HMD 152 generate electrical signals based on movement of the HMD 152 and send the electrical signals via the communication medium 112 to the computing device 136. Moreover, the one or more position and orientation measurement devices of the hand-held controller 154 generate electrical signals based on movement of the hand-held controller 154 and send the electrical signals via the communication medium 116 to the computing device 136. The processor of the computing device 136 receives the electrical signals from the HMD 152 and calculates a position and orientation of the HMD 152 based on the electrical signals. Similarly, the processor of the computing device 136 receives the electrical signals from the hand-held controller 154 and calculates a position and orientation of the hand-held controller 154 based on the electrical signals.

In some embodiments, in addition to the one or more position and orientation measurement devices, the camera 104 (FIG. 1A) is used to capture images of the hand-held controller 154 and the HMD 152. In these embodiments, each of the hand-held controller 154 and the HMD 152 has light sources or other markers.

In various embodiments, in addition to the one or more position and orientation measurement devices, the HMD 152 has the photosensors 132 and the hand-held controller 154 has the photosensors 142. Moreover, the system 150 includes the projectors 138A and 138B to determine the position and orientation of the HMD 152 and the hand-held controller 154.

Figure 2A:
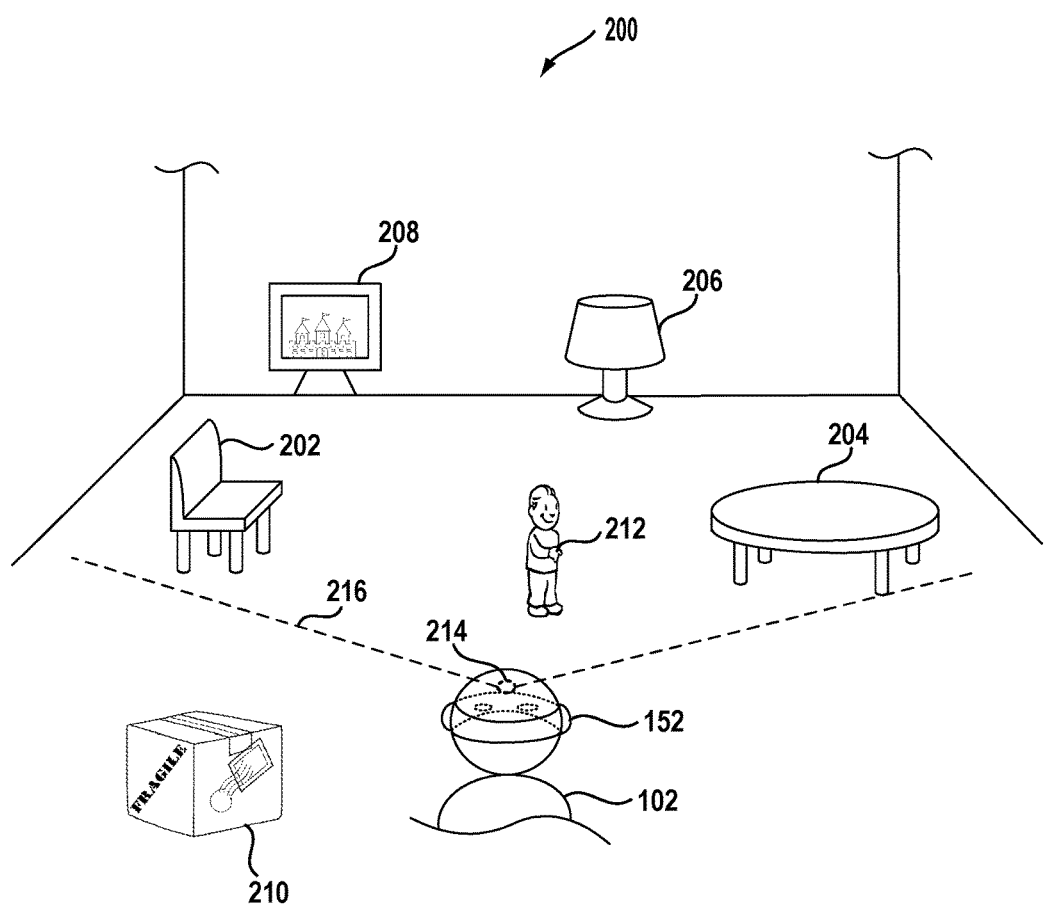
FIG. 2A is a diagram of an embodiment of an environment in which the user is located to play a video game.

FIG. 2A is a diagram of an embodiment of a real-world environment 200 in which the user 102 is located to play the video game. The real-world environment 200 includes real-world objects, such as, for example, a chair 202, a table 204, a lamp 206, a television 208, a box 210. The environment 200 also includes a spectator 212. The user 102 is wearing the HMD 152, which has a camera 214 having a lens that is facing the real-world environment 200. The camera 214 has an FOV 216, which is a portion of the real-world environment 200 that is viewed by the camera 214 to captures one or more images of the portion of the environment 200. For example, the camera 214 captures images of the spectator 212, the chair 202, the television 208, the lamp 206, and the table 204. The camera 214 cannot capture images of the box 210, which is outside the FOV 216. The spectator 212 is obstructing the FOV 216. For example, the camera 202 cannot determine a depth between the user 102 and the lamp 206 that is being obstructed from the FOV 216 by the spectator 212. A view of the lamp 206 by the camera 202 is being obstructed by the spectator 212. As another example, in an embodiment in which the proximity sensors are used instead of or in addition to the camera 202, the proximity sensors cannot generate electrical signals representing a distance and orientation of the user 102 from the lamp 206 that is being obstructed from the FOV 216 by the spectator 212.

FIG. 2B is a top-view of an embodiment of a real-world environment 220 in which the user 102 is located and outside-in tracking is performed by the camera 104. The environment 220 includes the user 102, the spectator 212, a sofa 222, the HMD 110, the hand-held controller 108, and the camera 104. The sofa 222 is an example of a real-world object. The camera 104 has an FOV 224, which is a view of the camera 104 for capturing images of the user 102, the spectator 212, the HMD 110, the hand-held controller 108, and the sofa 222. It should be noted that all real-world objects, e.g., the user 102, the spectator 212, the HMD 110, the hand-held controller 108, and the sofa 222, etc., are in the FOV 224.

The camera 104 also has a trackable FOV 226, which has a smaller volume than the FOV 224. For example, the trackable FOV 226 has a smaller surface area of a floor of the environment 220 compared to a surface area of the floor covered by the FOV 224. The trackable FOV 226 is a portion of the FOV 224. The trackable FOV 226 includes the user 102, the HMD 110, the hand-held controller 108, and the spectator 212. The camera 104, when operated, is able to capture images of the real-world objects within the trackable FOV 226. In some embodiments, the camera 104 cannot focus on real-world objects that are within the FOV 224 but outside the trackable FOV 226. The lack of focus does not allow the camera 104 to capture clear images of the real-world objects that are within the FOV 224 but outside the trackable FOV 226. The clear images pass a pre-determined threshold level of clarity of the images and unclear images do not pass the pre-determined threshold level. The threshold level is stored within a memory device of the camera 104 and is implemented by a processor of the camera 104. The camera 104 is able to focus on real-world objects that are within the trackable FOV 226 to capture images of the real-world objects.

The spectator 212 is not obstructing the HMD 110 and the hand-held controller 108 from the trackable FOV 226. For example, the HMD 110 is visible from the lens of the camera 104 to capture images of the HMD 110. As another example, the hand-held controller 108 is also visible from the lens of the camera 104 to capture images of the hand-held controller 108.

FIG. 2C is a top-view of the environment 220 in which the spectator 212 is obstructing the HMD 110 and the hand-held controller 108 from the trackable FOV 226 of the camera 104. The real-world objects, e.g., the user 102, the HMD 110, the hand-held controller 108, and the spectator 212, etc., are within the trackable FOV 226. However, the spectator 212 is standing in front of the hand-held controller 108 to block a view of one or more portions of the hand-held controller 108. The view of the hand-held controller 108 is from a lens of the camera 104. The camera 104 cannot capture an image of the one or more portions of the hand-held controller 108 when the view of the one or more portions of the hand-held controller 108 is blocked. Similarly, the spectator 212 is standing in front of the HMD 110 to block a view of one or more portions of the HMD 110. The view of the HMD 110 is from the lens of the camera 104. The camera 104 cannot capture an image of the one or more portions of the HMD 110 when the view of the one or more portions of the HMD 110 are blocked. For example, the processor of the computing device 136 receives an image of an FOV of the camera 104 from the camera 104 via the communication medium 114 and determines from the image whether a number of markers on the HMD 110, such as a number of markers on a front face of the HMD 110 facing the real-world environment, are lower than a pre-determined number of markers. The pre-determined number of markers are on a pre-determined portion, such as the front face, of the HMD 110. Upon determining that the number of markers in the image are lower than the pre-determined number of markers, the processor of the computing device 136 determines that one or more of the markers on the HMD 110 are occluded and the spectator 212 is obstructing the trackable FOV 226. On the other hand, upon determining that the number of markers are not lower than the pre-determined number of markers, such as match the pre-determined number of markers, the processor of the computing device 136 determines that the spectator 212 is not obstructing the trackable FOV 226.

FIG. 3A is a top-view of an embodiment of an environment 300 in which the user 102 is located and inside-out tracking is performed by the HMD 152. The environment 300 includes the user 102, the spectator 212, the sofa 222, the HMD 152, the hand-held controller 108, and the lamp 206. The camera 202 implemented within the HMD 152 has an FOV 304, which is a view of the camera 202 for capturing images of the lamp 206, the hand-held controller 108, and a wall 308. It should be noted that real-world objects, e.g., the lamp 206, and the hand-held controller 108, and the wall 308, etc., are in the FOV 304. However, remaining walls, e.g., a wall 308B, a wall 308C, and a wall 308D, etc., of the environment 300 are outside the FOV 304.

The camera 202 also has a trackable FOV 306, which has a smaller volume than the FOV 304. For example, the trackable FOV 306 has a smaller surface area of a floor of the environment 300 compared to a surface area of the floor covered by the FOV 304. The trackable FOV 306 is a portion of the FOV 304. The trackable FOV 306 includes the hand-held controller 108, and the wall 308B. The camera 202, when operated, is able to capture images of the real-world objects within the trackable FOV 306. In some embodiments, the camera 202 cannot focus on real-world objects that are within the FOV 304 but outside the trackable FOV 306. The lack of focus does not allow the camera 202 to capture clear images of the real-world objects that are within the FOV 304 but outside the trackable FOV 306. The clear images pass a pre-determined limit of clarity of the images and unclear images do not pass the pre-determined limit. The pre-determined limit is stored within a memory device of the camera 202 and is implemented by a processor of the camera 202. The camera 202 is able to focus on real-world objects that are within the trackable FOV 306 to capture images of the real-world objects.

The spectator 202 is not obstructing real-world objects, e.g., the wall 308A, etc., in the trackable FOV 306 and the unobstructed real-world objects are used by the camera 202 and the computing device 136 (FIG. 1C) to determine a position and orientation of the HMD 152. For example, the spectator 202 is outside the trackable FOV 306 to not obstruct electromagnetic waves emitted by the proximity sensor of the HMD 152 from reaching the wall 308A for reflection back to the HMD 152 or to not block a view of the wall 308A visible through the lens of the depth camera of the HMD 152. As another example, any electromagnetic waves emitted by the proximity sensor of the HMD 152 are reflected by the wall 308A towards the HMD 152 for being sensed by the proximity sensor when the spectator 212 is not within the trackable FOV 306. As yet another example, the lens of the camera 202 has a view of the wall 308A when the spectator 212 is not within the trackable FOV 306.

FIG. 3B is a top-view of the environment 300 in which the spectator 212 is obstructing the trackable FOV 306 of the HMD 152. The real-world objects, e.g., the hand-held controller 108 and the spectator 212, etc., are within the trackable FOV 306. However, the spectator 212 is standing in front of the hand-held controller 108 to block from the HMD 152 a view of one or more portions of the wall 308A. The view of the wall 308A is from the lens of the camera 202. The camera 202 cannot capture an image of the one or more portions of the wall 308A to allow the processor of the computing device 136 (FIG. 1C) to determine a position and orientation of the HMD 152 within the environment 300. Similarly, the spectator 212 is standing in front of the HMD 152 to block a view of one or more portions of the wall 308A. Similarly, the spectator 212 is blocking the electromagnetic waves that are emitted by the proximity sensor of the HMD 152 and the electromagnetic waves cannot reach a portion of the wall 308A to be reflected from the portion of the wall 308A towards the proximity sensors.

Figure 3C:
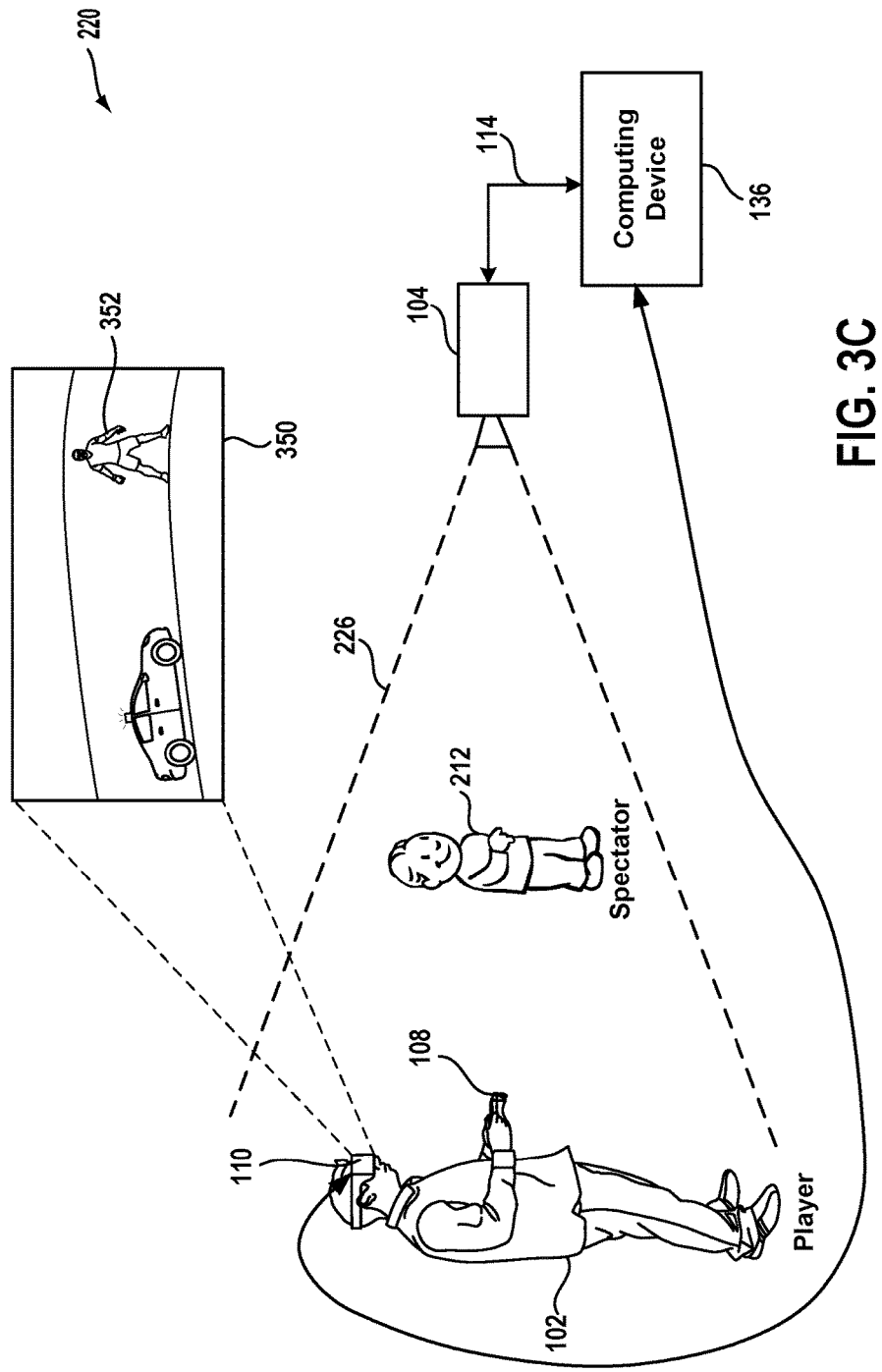
FIG. 3C is a view of an embodiment of an environment.

FIG. 3C is a view of an embodiment of the environment 220. The user 102 is wearing the HMD 110. On one or more display screens of the HMD 110, the processor of the HMD 110 renders an image 350 of the video game. In the image 350, there is an avatar 352 of the user 102. The trackable FOV 226 of the camera 104 is obstructed by the spectator 212, who is standing between the camera 104 and the user 102. For example, the camera 104 cannot capture an image of a portion of the HMD 110. To illustrate, the camera 104 cannot capture an image of any markers, e.g., light sources, reflective tape, etc., on the HMD 110. There is no line-of-sight between the camera 105 and one or more portions of the HMD 110. Moreover, as another example, the camera 104 cannot capture an image of a portion of the hand-held controller 108. There is no line-of-sight between the camera 105 and one or more portions of the hand-held controller 108.

Due to the obstruction by the spectator 212, the camera 104 cannot capture images of one or more portions of the HMD 110. During the time in which the camera 104 cannot capture the images of one or more portion of the HMD 110, the processor of the computing device 136 cannot use the images to calculate a position and orientation of the HMD 110.

Similarly, due to the obstruction by the spectator 212, the camera 104 cannot capture images of one or more portions of the hand-held controller 108. During the time in which the camera 104 cannot capture the images of one or more portion of the hand-held controller 108, the processor of the computing device 136 cannot use the images to calculate a position and orientation of the hand-held controller 108.

Figure 4A:
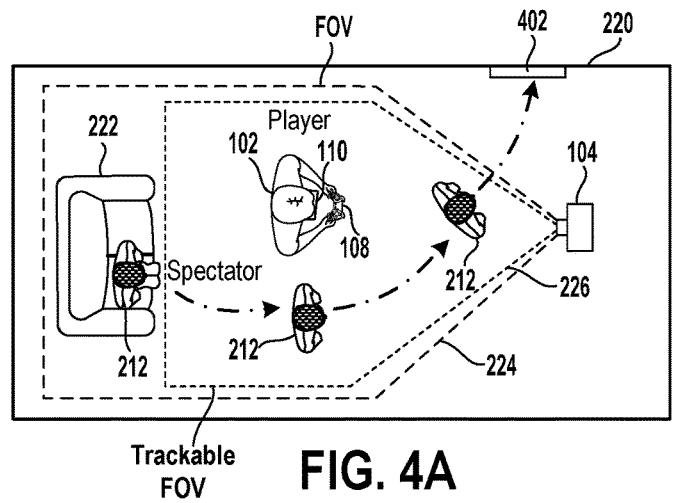
FIG. 4A is a diagram of an embodiment of an environment to illustrate a change in position of the spectator from a position that is not obstructing a trackable FOV of a camera to a position that is obstructing the trackable FOV.

FIG. 4A is a diagram of an embodiment of the environment 220 to illustrate a change in position of the spectator 212 from a position that is not obstructing the trackable FOV 226 of the camera 104 to a position that is obstructing the trackable FOV 226. When the user 102 is playing the video game that is displayed on the one or more display screens of the HMD 110, the spectator 212 is sitting on the sofa 222. After some time, the spectator 212 gets up and walks to a position besides the user 102. The spectator 212 continues walking to exit the environment 220 via a door 402. When the spectator 212 blocks a view of the camera 104 so that the camera 104 cannot view the one or more portions of the HMD 110, the trackable FOV 226 is obstructed by the spectator 212. Similarly, in some embodiments, when spectator blocks a view of the camera 104 so that the camera 104 cannot view the one or more portions of the hand-held controller 108, a portion of the trackable FOV 226 in which the hand-held controller 108 is located is obstructed by the spectator 212.

FIG. 4B is a diagram of an embodiment of a view 410 of the environment 220 from the lens of the camera 104. For example, the view 410 is displayed on a display device of the camera 104. The view 410 includes an image of the HMD 110, the hand-held controller 108, the user 102, the spectator 212, and the sofa 222. The HMD 110 has on its surface, markers, labeled as 412A, 412B, 412C, 412D, and 412E, to facilitate determination of a position and orientation of the HMD 110. In some embodiments, the markers 412A through 412E are a part of the HMD 110.

When the spectator 212 is within the FOV 224 but outside the trackable FOV 226, the camera 104 detects a face of the spectator 212 to identify the spectator 212 to the user 102. In some embodiments, in addition to or instead of capturing the image of the face of the spectator 212 when the spectator 212 is outside the trackable FOV 226 but in the FOV 224, the camera 104 detects the face of the spectator 212 and captures an image of the face of the spectator 212 after the spectator 212 is within the trackable FOV 226.

The camera 104 captures an image of the face of the spectator 212 and sends the image via the communication medium 114 (FIG. 1A) to the computing device 136 (FIG. 1B). The processor of the computing device 136 determines from the image of the face whether the image matches a pre-stored image in a user identification (ID) database within a memory device of the computing device 136 or within a cloud computing network to which the HMD 110 (FIG. 1A), HMD 132 (FIG. 1B), or the HMD 152 (FIG. 1C) is coupled. The HMD 110, the HMD 132, or the HMD 152 is coupled to the cloud computing network via a router. The processor of the computing device 136 upon determining that the image of the face matches the pre-stored image, identifies the spectator 212 as having the user ID that is associated with, e.g., mapped to, linked with, corresponding to, etc., to the pre-stored image. The processor of the computing device 136 sends the user ID via the communication medium 112 (FIG. 1A) to the HMD 110. The processor of the HMD 110 upon receiving the user ID displays the user ID on the one or more display screens of the HMD 110 so that the user 102 can recognize the spectator 212 and is able to determine that the spectator 212 is a reason for lack of determination of position and orientation of the HMD 110. The lack of determination of the position and orientation affects the game state. For example, the processor of the computing device 136 cannot determine the next game state without first determining the position and orientation of the HMD 110. The position and orientation of the HMD 110 are input to the game code to determine the next game state.

Figure 4C:
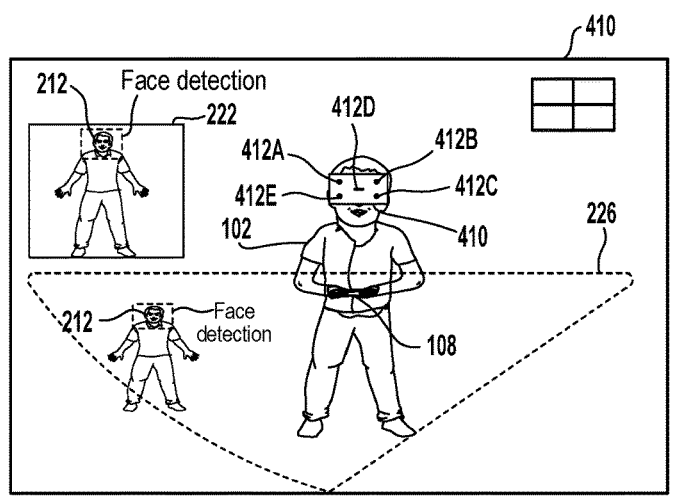
FIG. 4C is a diagram of an embodiment to illustrate a view of a camera having a focus area and another focus area.
Figure 4C:
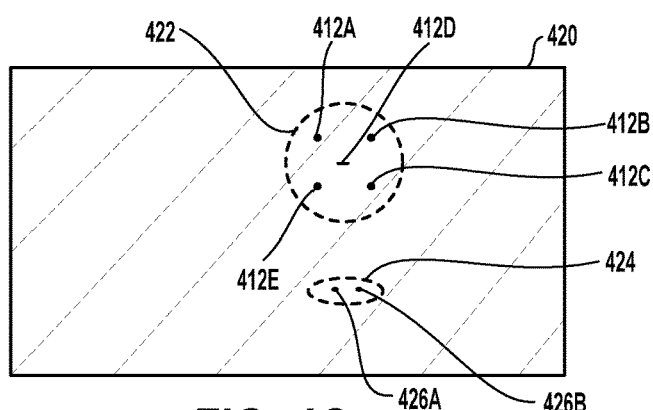

FIG. 4C is a diagram of an embodiment to illustrate a view 420 of the camera 104 having a focus area 422 and another focus area 424. The focus area 422 includes an image of the markers 412A through 412D and an image of markers 426A and 426B. The markers 426A and 426B are located on a surface of the hand-held controller 108. Examples of the markers 426A and 426B include light sources and reflective tape. In some embodiments, the markers 426A through 426B are a part of the hand-held controller 108. The view 420 is a view through the lens of the camera 104. For example, the view 420 is displayed by the processor of the camera 104 on the display device of the camera 104.

The camera 104 is focused on the focus areas 422 and 424. For example, an ultrasonic emitter of the camera 104 generates sound waves and sends the sound waves towards the FOV 224. The sound waves are reflected from the HMD 110, the hand-held controller 108, and the spectator 212 when the HMD 110, the hand-held controller 108, and the spectator 212 are within the FOV 224. A sound detector of the camera 104 detects the reflected sound waves to generate electrical signals. The electrical signals are sent from the sound detector to the processor of the camera 104. The processor of the camera 104 determines whether an amplitude of the sound waves reflected from the HMD 110 and the controller 108 is greater than an amplitude of the sound waves reflected from the spectator 212. Upon determining that the amplitude of the sound waves reflected from the HMD 110 is greater than the amplitude of the sound waves reflected from the spectator 212, the processor of the camera 104 controls an exposure control mechanism of the camera 104 to focus on an image of the markers 412A through 412E. To illustrate, the processor of the camera 104 sends a signal to an aperture driver within the camera 104 to control movement of a motor, which rotates to change a position of an aperture diaphragm within the camera 104 to change a diameter of an aperture of the camera 104. The motor is located within the camera 104. Moreover, the processor of the camera 104 sends a signal to a shutter driver within the camera 104 to provide a current signal to a drive mechanism of the camera 104, and the drive mechanism generates an amount of electromagnetic field, which changes a speed with which a shutter of the camera 104 is open and closed. The control of the aperture diaphragm and the shutter diaphragm helps achieve focus on the focus area 422. Similarly, upon determining that the amplitude of the sound waves reflected from the hand-held controller 108 is greater than the amplitude of the sound waves reflected from the spectator 212, the processor controls the exposure control mechanism to focus on an image of the markers 426A and 426B to generate the focus area 424.

When the camera 104 is focused on the focus areas 422 and 424, a photodetector system, which includes multiple photosensors, captures images of the markers 412A through 412E and the markers 426A and 426B to generate electrical signals, which are sent from the photodetector system to the processor of the camera 104. The processor of the camera 104 sends the electrical signals to the processor of the computing system 136 (FIG. 1B) via the communication medium 114 (FIG. 1A). From the electrical signals, the processor of the computing system 136 determines a position and orientation of the HMD 110 and a position and orientation of the hand-held controller 108. For example, an intensity of an electrical signal defines a position of the HMD 110. To illustrate, when a first value of the intensity is greater than a second value of the intensity, a position of the HMD 110 when the first value is detected by the photodetector system is closer to the camera 104 than a position of the HMD 110 when the second value is detected by the photodetector system. Moreover, as an example, an orientation of the markers 412A through 412E in the image that is captured by the camera 104 is the same as an orientation of the HMD 110 in the real-world environment 220. Similarly, as an example, an intensity of an electrical signal defines a position of the hand-held controller 108. To illustrate, when a first value of the intensity is greater than a second value of the intensity, a position of the hand-held controller 108 when the first value is detected by the photodetector system is closer to the camera 104 than a position of the hand-held controller 108 when the second value is detected by the photodetector system. Moreover, as an example, an orientation of the markers 426A and 426B in the image that is captured by the camera 104 is the same as an orientation of the hand-held controller 108 in the real-world environment 220.

In some embodiments, the HMD 110 includes any other number, e.g., three, seven, ten, twenty, etc., of markers, to allow determination of position and orientation of the HMD 110. Similarly, in various embodiments, the hand-held controller 108 includes any other number, e.g., three, seven, ten, twenty, etc., of markers, to allow determination of position and orientation of the hand-held controller 108.

In various embodiments, markers on the HMD 110 are placed in a different arrangement than that illustrated in FIG. 4B. Similarly, in several embodiments, markers on the hand-held controller 108 are placed in a different arrangement than that illustrated in FIG. 4B.

Figure 5A:
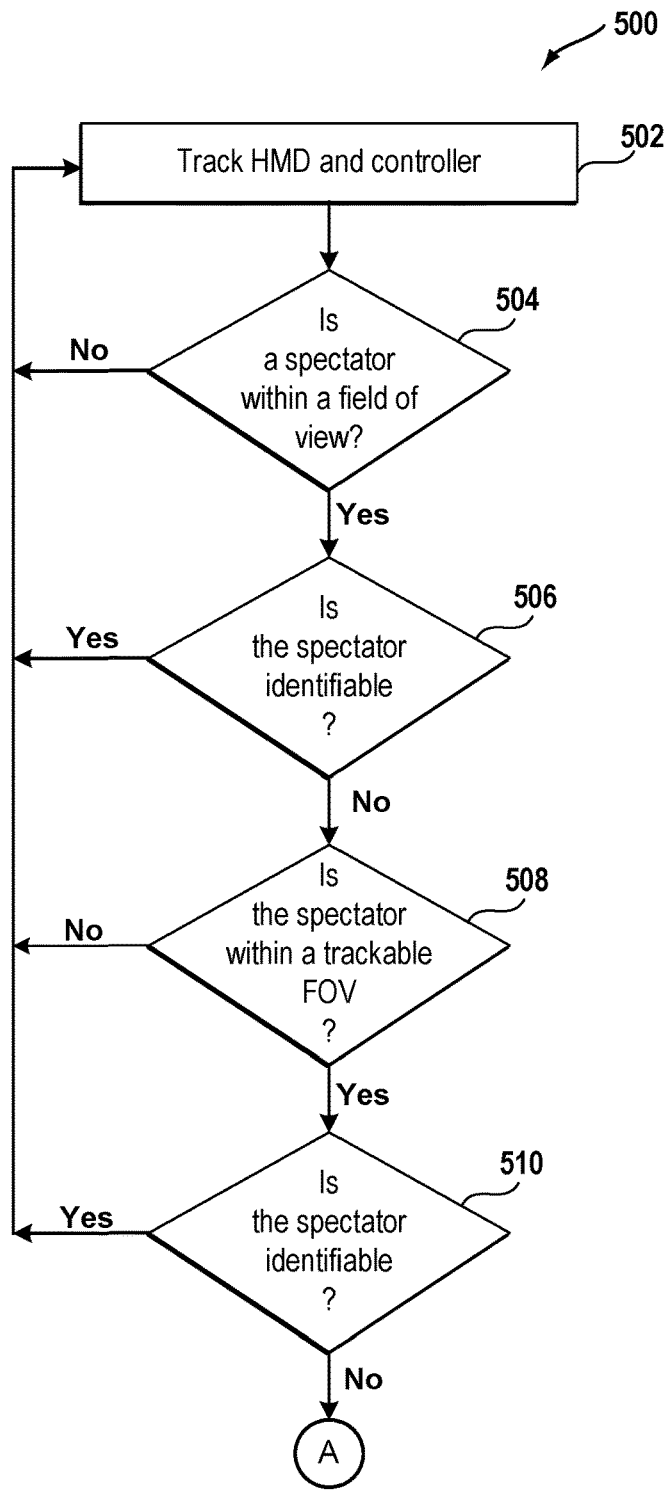
FIG. 5A is a flowchart of an embodiment of a method for notifying the user that the spectator is obstructing a trackable FOV.

FIG. 5A is a flowchart of an embodiment of a method 500 for notifying the user 102 that the spectator is obstructing the trackable FOV 226. The method 500 is executed by the processor of the computing device 136 (FIGS. 1B & 1C).

In an operation 502 of the method 500, the processor of the computing device 136 tracks an HMD and a hand-held controller. For example, the processor of the computing device 136 determines a position and orientation of the HMD 110 and a position and orientation of the hand-held controller 108 (FIG. 1A), or a position and orientation of the HMD 132 and a position and orientation of the hand-held controller 134 (FIG. 1B), and a position and orientation of the HMD 152 and a position and orientation of the hand-held controller 154 (FIG. 1C). An example of determining the position and orientation of the HMD 110 and of the hand-held controller 108 is provided above. As another example, the processor of the computing device 136 sends a signal via the communication medium 114 (FIG. 1A) to the processor of the camera 104 to capture an image of the HMD 110 and the hand-held controller 108. The processor of the camera 104 upon receiving the signal, commands the photodetector system to capture the image. The photodetector system generates electrical signals from the light reflected from the HMD 110 and the hand-held controller 108. The electrical signals are processed to generate image data of the image, and the image data is sent by the processor of the camera 104 via the communication medium 114 to the processor of the computing device 136. The processor of the computing device determines a position and orientation of the HMD 110 and the hand-held controller 108 from the image data in a manner described above, e.g., by using intensity of light, etc. The image data is data that is rendered to display the image. An example of tracking the HMD and the hand-held controller is illustrated using FIG. 4C. The focus on the HMD and the hand-held controller is achieved to track the HMD and the hand-held controller.

In an operation 504 of the method 500, it is determined whether the spectator 212 (FIG. 4A) is within the FOV 224 (FIG. 4A). For example, the processor of the computing device 136 sends an instruction to the processor of the camera 104 via the communication medium 114 (FIG. 1A) to send a command to the ultrasonic emitter to generate and send sound waves towards the real-world environment 220. Upon receiving the instruction, the processor sends the command. Upon receiving the command, the ultrasonic emitter generates and emits the sound waves. The sound waves are reflected from the spectator 212 towards the sound detector of the camera 104. The sound detector generates electrical signals from the reflected sound waves and sends the electrical signals to the processor of the camera 104. The processor of the camera 104 sends the electrical signals via the communication medium 114 to the processor of the computing device 136. The processor of the computing device 136 determines whether amplitudes of the electrical signals are greater than a pre-determined amplitude threshold. Upon determining that the amplitudes of the electrical signals are greater than the pre-determined amplitude threshold, the processor of the computing device 136 determines that the spectator is within the FOV 224. On the other hand, upon determining that the amplitudes of the electrical signals are not greater than the pre-determined amplitude threshold, the processor of the computing device 136 determines that the spectator is not within, e.g., outside, etc., the FOV 224. As another example, the processor of the computing device 136 sends an instruction to the processor of the camera 202 (FIG. 2A) via the communication medium 112 (FIG. 1C) to send a command to the ultrasonic emitter of the camera 202 to generate and send sound waves towards the real-world environment 300 (FIG. 3A). Upon receiving the instruction, the processor sends the command. Upon receiving the command, the ultrasonic emitter of the camera 202 generates and emits the sound waves. The sound waves are reflected from the spectator 212 towards the sound detector of the camera 202. The sound detector of the camera 202 generates electrical signals from the reflected sound waves and sends the electrical signals to the processor of the camera 202. The processor of the camera 202 sends the electrical signals via the communication medium 112 to the processor of the computing device 136. The processor of the computing device 136 determines whether the spectator 212 is within or outside the FOV 304 in a manner described above for determining whether the spectator 212 is within or outside the FOV 224.

Upon determining that the spectator 212 is not within the FOV 224, the operation 502 is repeated. For example, the processor of the computing device 136 continues to track the HMD 110 and the hand-held controller 108 upon determining that the spectator 212 is not within the FOV 224.

On the other hand, upon determining that the spectator 212 is within the FOV 224, it is determined in an operation 506 of the method 500 whether the spectator 212 is identifiable. For example, upon determining that the spectator 212 is within the FOV 224, the processor of the computing device 136 instructs the processor of the camera 104 via the communication medium 114 to capture an image of the real-world environment 220 including the spectator 212. From the image of the real-world environment 220 that is captured by the camera 104, the processor of the computing device 136 determines whether a quality of a representation of the spectator 212 within the image is greater a pre-determined quality threshold. For example, the processor of the computing device 136 determines whether the quality of the representation of the spectator 212 is sufficient to distinguish the spectator 212 from a background within the image and from other real-world objects captured in the image. To illustrate, the processor of the computing device 136 determines whether an outline of the face of the spectator 212 is distinguished from the background in the image. The background of the image includes walls of the real-world environment 220, the sofa 222, and other real-world objects, e.g., windows, paintings, etc., in the real-world environment 220. Upon determining that the quality of the representation of the spectator 212 is sufficient to distinguish the spectator 212 from the background within the image and from the other real-world objects captured in the image, the processor of the computing device 136 determines that the quality of the of the representation of the spectator 212 exceeds the pre-determined quality threshold. On the other hand, upon determining that the quality of the representation of the spectator 212 is not sufficient to distinguish the spectator 212 from the background within the image and from the other real-world objects captured in the image, the processor of the computing device 136 determines that the quality of the of the representation of the spectator 212 does not exceed the pre-determined quality threshold and the spectator 212 is not identifiable. Upon determining that the quality of the representation of the spectator 212 exceeds the pre-determined quality threshold, the processor of the computing device 136 determines whether the representation of the spectator matches the pre-stored image in the user ID database. Moreover, upon determining that the representation of the spectator matches the pre-stored image in the user ID database, the processor of the computing device 136 accesses the user ID of the spectator 212 and determines that the spectator 212 is identifiable.

As another example, upon determining that the spectator 212 is within the FOV 224, the processor of the computing device 136 instructs the processor of the HMD 110 via the communication medium 112 (FIG. 1A) to command a sound recorder of the HMD 110 to capture an audio of the spectator 212 when the spectator 212 utter a sound. The processor of the sends the command to a microphone of the HMD 110 to capture the audio of the spectator 212. The microphone captures the audio and converts the audio into electrical signals, which are converted by an analog-to-digital converter (A-D converter) of the HMD 110 from an analog form to a digital form and the digital form is stored as voice data in an audio memory device of the HMD 110. The processor of the HMD 110 accesses the voice data from the audio memory device of the HMD 110 and sends the voice data via the communication medium 112 to the processor of the computing device 136. The processor of the computing device 136 determines whether the voice data matches pre-stored voice data in the user ID database. To illustrate, the processor of the computing device 136 determines whether a parameter, e.g., tone, pitch, etc., of the voice data matches the parameter of pre-stored voice data, which is pre-stored in the user ID database of the memory device of the computing device 136. The pre-stored voice data is associated with, e.g., has a one-to-one relationship with, is linked to, has a mapping with, etc., the user ID. Upon determining that the parameter matches the pre-stored parameter in the user ID database, the processor of the computing device 136 accesses the user ID of the spectator 212 and determines that the spectator 212 is identifiable. Moreover, upon determining that the parameter does not match the pre-stored parameter in the user ID database, the processor of the computing device 136 determines that the spectator 212 is not identifiable.

As yet another example, both the representation of the spectator 212 and the voice data of the spectator 212 are used to determine whether the spectator 212 is identifiable. For example, upon determining that the quality of the representation of the spectator 212 is not sufficient to distinguish the spectator 212 from the background within the image and from the other real-world objects captured in the image and/or upon determining that the parameter associated with the voice data does not match the pre-stored parameter in the user ID database, the processor of the computing device 136 determines that the spectator 212 is not identifiable. On the other hand, upon determining that the representation of the spectator matches pre-stored image in the user ID database and that the parameter associated with the voice data matches the pre-stored parameter in the user ID database, the processor of the computing device 136 determines that the spectator 212 is identifiable.

Upon determining that the spectator 212 is identifiable in the operation 506, the operation 502 of tracking the HMD 110 and the hand-held controller 108 is repeated. On the other hand, upon determining that the spectator 212 is not identifiable in the operation 506, an operation 508 of the method 500 is executed. For example, the processor of the computing device 136 sends an instruction to the processor of the camera 104 via the communication medium 114 (FIG. 1A) to send a command to the ultrasonic emitter to generate and send sound waves towards the real-world environment 220. Upon receiving the instruction, the processor of the camera 104 sends the command. Upon receiving the command, the ultrasonic emitter generates and emits the sound waves. The sound waves are reflected from the spectator 212 towards the sound detector of the camera 104. The sound detector generates electrical signals from the reflected sound waves and sends the electrical signals to the processor of the camera 104. The processor of the camera 104 sends the electrical signals via the communication medium 114 to the processor of the computing device 136. The processor of the computing device 136 determines whether amplitudes of the electrical signals are greater than a pre-determined amplitude limit.

Upon determining that the amplitudes of the electrical signals are greater than the pre-determined amplitude limit, the processor of the computing device 136 determines that the spectator is within the trackable FOV 226. On the other hand, upon determining that the amplitudes of the electrical signals are not greater than the pre-determined amplitude limit, the processor of the computing device 136 determines that the spectator is not within, e.g., outside, etc., the trackable FOV 226. It should be noted that in some embodiments, the pre-determined amplitude limit associated with the trackable FOV 226 is greater in magnitude than the pre-determined amplitude threshold associated with the FOV 224. For example, amplitudes of the electrical signals reflected from the spectator 212 that exceed the pre-determined amplitude threshold associated with the FOV 224 may not exceed the pre-determined amplitude limit associated with the trackable FOV 226. In this case, the spectator 212 is within the FOV 224 but outside the trackable FOV 226.

As another example, the processor of the computing device 136 sends an instruction to the processor of the camera 202 (FIG. 2A) of the HMD 152 via the communication medium 112 (FIG. 1B) to send a command to the ultrasonic emitter of the camera 202 to generate and send sound waves towards the real-world environment 300. Upon receiving the instruction, the processor of the camera 202 sends the command. Upon receiving the command, the ultrasonic emitter generates and emits the sound waves. The sound waves are reflected from the spectator 212 towards the sound detector of the camera 202. The sound detector generates electrical signals from the reflected sound waves and sends the electrical signals to the processor of the camera 202. The processor of the camera 202 sends the electrical signals via the communication medium 112 to the processor of the computing device 136 for determination whether the spectator 212 is within the trackable FOV 306 the trackable FOV 306. The determination whether the spectator 212 is within the trackable FOV 306 is made in the same manner as that described above for determining whether the spectator 212 is within the trackable FOV 226.

Upon determining that the spectator 212 is not within the trackable FOV 226, the operation 502 is repeated. On the other hand, upon determining that the spectator 212 is within the trackable FOV 226, in an operation 510 of the method 500, it is determined whether the spectator 212 is identifiable when within the trackable FOV 226. For example, upon determining that the spectator 212 is within the trackable FOV 226, the processor of the computing device 136 instructs the processor of the camera 104 via the communication medium 114 to capture an image of the real-world environment 220 including the spectator 212. From the image of the real-world environment 220 that is captured by the camera 104, the processor of the computing device 136 determines whether a quality of a representation of the spectator 212 within the image is greater the pre-determined quality threshold, as is described above in the operation 506. Upon determining that the quality of the representation of the spectator 212 exceeds the pre-determined quality threshold, the processor of the computing device 136 determines whether the representation of the spectator matches the pre-stored image in the user ID database. Moreover, upon determining that the representation of the spectator matches pre-stored image in the user ID database, the processor of the computing device 136 accesses the user ID of the spectator 212 and determines that the spectator 212 is identifiable.

As another example, upon determining that the spectator 212 is within the trackable FOV 226, the processor of the computing device 136 instructs the processor of the HMD 110 via the communication medium 112 (FIG. 1A) to command the sound recorder of the HMD 110 to capture an audio of the spectator 212 when the spectator 212 utters a sound. The processor of the sends the command to a microphone of the HMD 110 to capture the audio of the spectator 212. The same process described above in the operation 506 is executed. To illustrate, upon determining that the parameter associated with the voice data generated from the audio of the spectator 212 matches the pre-stored parameter in the user ID database, the processor of the computing device 136 accesses the user ID of the spectator 212 and determines that the spectator 212 is identifiable. Moreover, upon determining that the parameter does not match the pre-stored parameter in the user ID database, the processor of the computing device 136 determines that the spectator 212 is not identifiable.

As yet another example, both the representation of the spectator 212 and the voice data of the spectator 212 are used to determine whether the spectator 212 is identifiable as is described above in the operation 506.

Upon determining that the spectator 212 is identifiable in the operation 510, the operation 502 of tracking the HMD 110 and the hand-held controller 108 is repeated. On the other hand, upon determining that the spectator 212 is not identifiable in the operation 510, an operation 512, described with reference to FIG. 5B, of the method 500 is performed.

Figure 5B:
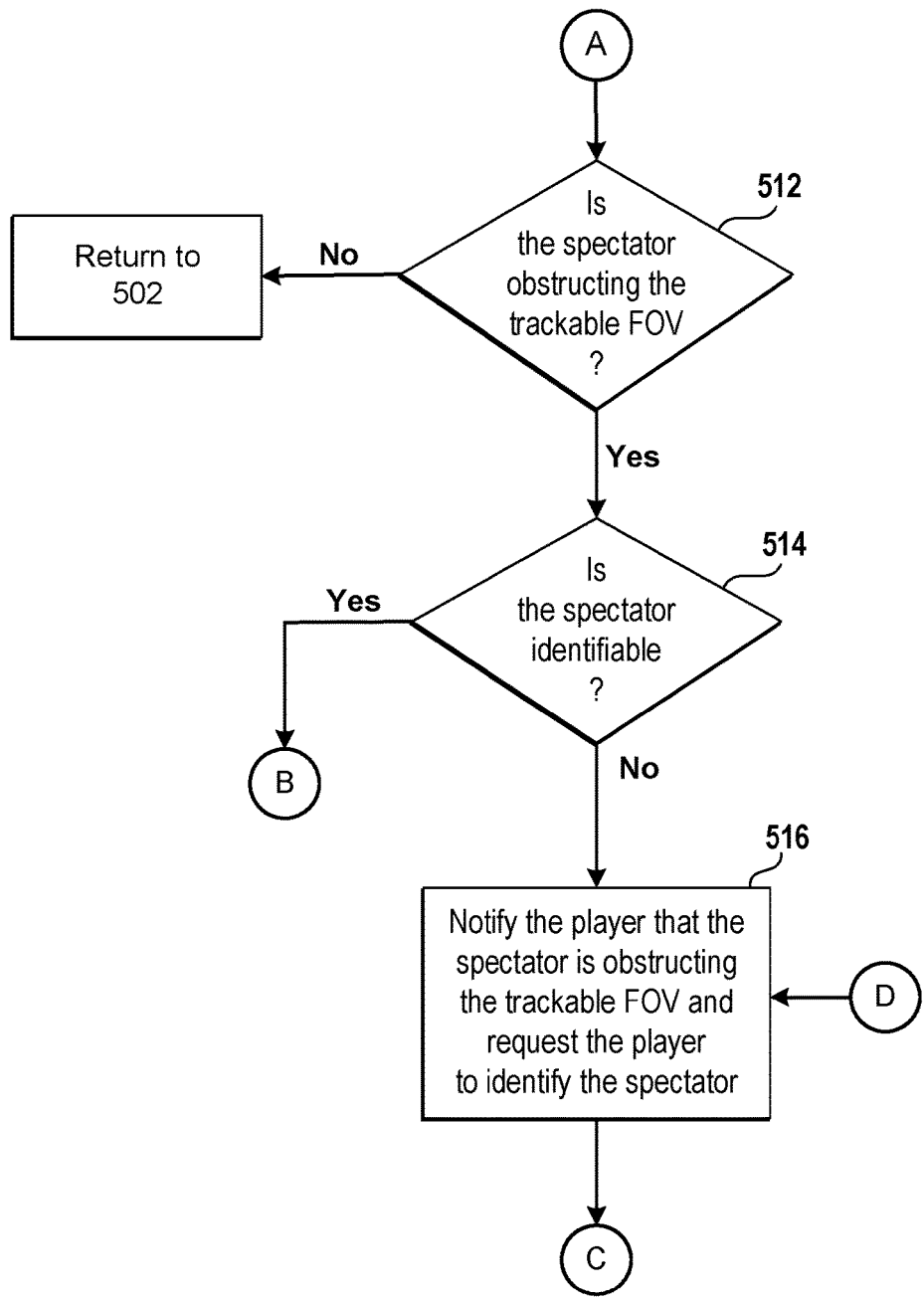
FIG. 5B is a continuation of the flowchart of the method of FIG. 5A.

FIG. 5B is a continuation of the flowchart of the method 500 of FIG. 5A. In the operation 512, it is determined whether the spectator 212 is obstructing the trackable FOV 226 of the camera 104. For example, it is determined whether the spectator 212 is blocking light reflected from the marker 412A, or the marker 412B, or the marker 412C, or the marker 412D, or the marker 412E, or a combination of two or more of the markers 412A, 412B, 412C, 412D, and 412E. To illustrate, the camera 104 captures an image that includes a representation of the spectator 212 and of one or more of the markers 412A through 412E, and sends the image to the processor of the computing device 136. The processor of the computing device 136 determines whether any portion of the marker 412A, or the marker 412B, or the marker 412C, or the marker 412D, or the marker 412E, or a combination of two or more of the markers 412A, 412B, 412C, 412D, and 412E is captured in the image. The processor compares a shape of the marker 412A, or the marker 412B, or the marker 412C, or the marker 412D, or the marker 412E captured in the image with that of a pre-stored shape of the marker. It should be noted that in some embodiments, all the markers 412A through 412E have the same shape. Upon determining that the shape of a portion of the marker captured in the image does not match the pre-stored shape of the marker, the processor of the computing device 136 determines that the image does not include the entire marker and that a portion of the marker is occluded by the spectator 212. On the other hand, upon determining that the shape of the marker 412A, 412B, 412C, 412D, or 412E in the image matches the pre-stored shape of the marker, the processor of the computing device 136 determines that the image includes the entire marker. The processor of the computing device 136 determines whether a number of the markers in the image for which the shape of each of the markers 412A, 412B, 412C, 412D, and 412E matches the pre-stored shape is equal to a pre-stored number. Upon determining that the number of the markers 412A, 412B, 412C, 412D, and 412E in the image for which the shape of each of the markers 412A, 412B, 412C, 412D, and 412E matches the pre-stored shape is equal to the pre-stored number, the processor determines of the computing device 136 determines that the spectator 212 is not obstructing the HMD 110 in the trackable FOV 226. It should be noted that the pre-stored shape and the pre-stored number are stored within the memory device of the computing device 136.

As another illustration, the camera 104 captures an image that includes a representation of the spectator 212 and of the HMD 110, and sends the image to the processor of the computing device 136. The processor of the computing device 136 determines whether any portion of the HMD 110 is captured in the image. The processor compares a shape of the HMD 110 captured in the image with that of a pre-stored shape of the HMD 110. Upon determining that the shape of a portion of the HMD 110 captured in the image does not match the pre-stored shape of the HMD 110, the processor of the computing device 136 determines that the image does not include the entire HMD 110 and that a portion of the HMD 110 is occluded by the spectator 212. On the other hand, upon determining that the shape of the HMD 110 in the image matches the pre-stored shape of the HMD 110, the processor of the computing device 136 determines that the image includes the entire HMD 110. Upon determining that the image includes the entire HMD 110, the processor of the computing device 136 determines that the spectator 212 is not obstructing the HMD 110 in the trackable FOV 226. On the other hand upon determining that the image does not include the entire HMD 110, the processor of the computing device 136 determines that the spectator 212 is obstructing the HMD 110 in the trackable FOV 226.

As another example, it is determined whether the spectator 212 is blocking light reflected from the marker 426A, or the marker 426B, or both the markers 426A and 426B. To illustrate, the camera 104 captures an image that includes a representation of the spectator 212 and the marker 426A and/or the marker 426B, and sends the image to the processor of the computing device 136. The processor of the computing device 136 determines whether any portion of the marker 426A, or the marker 426A, or both the markers 426A and 426B is captured in the image. The processor compares a shape of a marker captured in the image with that of a pre-determined shape of the marker. Upon determining that the shape of the marker 426A or 426B captured in the image does not match the pre-determined shape of the marker, the processor of the computing device 136 determines that the image does not include the entire marker and that a portion of the marker is occluded by the spectator 212. On the other hand, upon determining that the shape of the marker 426A or 426B in the image matches the pre-determined shape of the marker, the processor of the computing device 136 determines that the image includes the entire marker. The processor of the computing device determines whether a number of the markers in the image for which the shape of each of the markers 426A and 426B matches the pre-determined shape is equal to a pre-determined number of the markers. Upon determining that the number of the markers 426A and 426B in the image for which the shape of each of the markers 426A and 426B matches the pre-determined shape is equal to the pre-determined number, the processor determines of the computing device 136 determines that the spectator 212 is not obstructing the hand-held controller 108 in the trackable FOV 226. It should be noted that the pre-determined shape and the pre-determined number are stored within the memory device of the computing device 136.

As another illustration, the camera 104 captures an image that includes a representation of the spectator 212 and of the hand-held controller 108, and sends the image to the processor of the computing device 136. The processor of the computing device 136 determines whether any portion of the hand-held controller 108 is captured in the image. The processor compares a shape of the hand-held controller 108 captured in the image with that of a pre-stored shape of the hand-held controller 108. Upon determining that the shape of a portion of the hand-held controller 108 captured in the image does not match the pre-stored shape of the hand-held controller 108, the processor of the computing device 136 determines that the image does not include the entire hand-held controller 108 and that a portion of the hand-held controller 108 is occluded by the spectator 212. On the other hand, upon determining that the shape of the hand-held controller 108 in the image matches the pre-stored shape of the hand-held controller 108, the processor of the computing device 136 determines that the image includes the entire hand-held controller 108. Upon determining that the image includes the entire hand-held controller 108, the processor of the computing device 136 determines that the spectator 212 is not obstructing the hand-held controller 108 in the trackable FOV 226. On the other hand upon determining that the image does not include the entire hand-held controller 108, the processor of the computing device 136 determines that the spectator 212 is obstructing the hand-held controller 108 in the trackable FOV 226.

As another example, it is determined whether light that is emitted by the projectors 138A and 138B (FIG. 1B) is not detected by the photosensors 132 (FIG. 1B) of the HMD 132 (FIG. 1B). To illustrate, the processor of the computing device 136 (FIG. 1B) determines whether electrical signals are not received from one or more of the photosensors 140 for greater than a pre-determined period of time. The electrical signals are generated by the one or more of the photosensors 140 when light that is emitted by the projectors 138A and 138B is detected by the photosensors 140. The one or more of the photosensors 140 do not generate the electrical signals when the spectator 212 is obstructing a trackable FOV of one or more of the projectors 138A and 138B. The electrical signals, when generated, are sent from the photosensors 140 of the HMD 132 via the communication medium 112 (FIG. 1B) to the processor of the computing device 136. However, when the electrical signals are not generated by the one or more of the photosensors 140, there is no transmission of the electrical signals, and therefore, no reception of the electrical signals by the processor of the computing device 136. Upon determining that the electrical signals are not received from the one or more of the photosensors 140 for greater than the pre-determined period of time, the processor of the computing device 136 determines that the spectator 212 is obstructing the trackable FOV of the one or more of the projectors 138A and 138B.

As another example, the camera 202 (FIG. 2A) of the HMD 152 captures an image of the real-world environment 300 in front of the camera 202. The image includes an image of the spectator 212. The processor of the HMD 152 sends the image via the communication medium 112 to the processor of the computing device 136. The processor of the computing device 136 determines from the image and a pre-defined shape, e.g., a shape of a person, a shape of a man, a shape of a woman, etc., stored in the memory device of the computing device 136 that the image includes a representation of the spectator 212. For example, the processor of the computing device 136 compares a shape of the representation of the spectator 212 within the image with the pre-defined shape, and upon determining that there is a match between the shape and the pre-defined shape, the processor determines that the image includes the representation of the spectator 212. On the other hand, upon determining that the match does not occur, the processor of the computing device 136 determines that the image does not include the representation of the spectator 212. The processor of the computing device 136 determines that the spectator 212 is obstructing the trackable FOV 306 (FIGS. 3A & 3B) upon determining that the image includes the representation of the spectator 212. On the other hand, upon determining that the image does not include the representation of the spectator 212, the processor of the computing device 136 determines that the spectator 212 is not obstructing the trackable FOV 306.

Upon determining that the spectator 212 is not obstructing the HMD 110 and/or the hand-held controller 108 in the trackable FOV 226, the processor of the computing device 136 continues to perform the operation 502 of tracking the HMD 110 and the hand-held controller 108. On the other hand, upon determining that the spectator 212 is obstructing the HMD 110 and/or the hand-held controller 108 in the trackable FOV 226, in an operation 514 of the method 500, it is determined whether the spectator 512 is identifiable. For example, upon determining that the spectator 212 is obstructing the HMD 110 and/or the hand-held controller 108 in the trackable FOV 226, the processor of the computing device 136 instructs the processor of the camera 104 via the communication medium 114 to capture an image of the real-world environment 220 including the spectator 212. From the image of the real-world environment 220 that is captured by the camera 104, the processor of the computing device 136 determines whether a quality of a representation of the spectator 212 within the image is greater the pre-determined quality threshold, as is described above in the operation 506. Upon determining that the quality of the representation of the spectator 212 exceeds the pre-determined quality threshold, the processor of the computing device 136 determines whether the representation of the spectator 212 matches the pre-stored image in the user ID database. Moreover, upon determining that the representation of the spectator 212 matches the pre-stored image in the user ID database, the processor of the computing device 136 accesses the user ID of the spectator 212 and determines that the spectator 212 is identifiable.

As another example, upon determining that the spectator 212 is obstructing the HMD 110 and/or the hand-held controller 108 in the trackable FOV 306 (FIG. 3A), the processor of the computing device 136 instructs the processor of the camera 202 (FIG. 2A) via the communication medium 112 to capture an image of the real-world environment 300 (FIG. 3A) including the spectator 212. From the image of the real-world environment 300 that is captured by the camera 202, the processor of the computing device 136 determines whether a quality of a representation of a face of the spectator 212 within the image is greater the pre-determined quality threshold, as is described above in the operation 506. It should be noted that the spectator 212 is proximate to the HMD 152 when the representation of the face of the spectator 212 within the image is greater the pre-determined quality threshold. Upon determining that the quality of the representation of the face of the spectator 212 exceeds the pre-determined quality threshold, the processor of the computing device 136 determines whether the representation of the face of the spectator 212 matches the pre-stored image in the user ID database. Moreover, upon determining that the representation of the face of the spectator 212 matches the pre-stored image in the user ID database, the processor of the computing device 136 accesses the user ID of the spectator 212 and determines that the spectator 212 is identifiable.

As yet another example, upon determining that the spectator 212 is obstructing the HMD 110 and/or the hand-held controller 108 in the trackable FOV 226, the processor of the computing device 136 instructs the processor of the HMD 110 or the HMD 140 via the communication medium 112 (FIG. 1A) to command the sound recorder of the HMD 110 or the HMD 140 (FIG. 1B) to capture an audio of the spectator 212 when the spectator 212 utters a sound. The processor of the HMD 110 sends the command to a microphone of the HMD 110 or the HMD 140 to capture the audio of the spectator 212 to generate captured audio data. The captured audio data is sent from the processor of the HMD 110 or the HMD 140 to the processor of the computing device 136 via the communication medium 112. The same process described above in the operation 506 is executed thereafter. To illustrate, upon determining that the parameter associated with the voice data generated from the audio of the spectator 212 matches the pre-stored parameter in the user ID database, the processor of the computing device 136 accesses the user ID of the spectator 212 and determines that the spectator 212 is identifiable. Moreover, upon determining that the parameter does not match the pre-stored parameter in the user ID database, the processor of the computing device 136 determines that the spectator 212 is not identifiable.

As yet another example, both the representation of the spectator 212 and the voice data of the spectator 212 are used to determine whether the spectator 212 is identifiable as is described above in the operation 506.

As another example, the processor of the camera 104 sends a signal to the aperture driver within the camera 104 to control movement of the motor, which rotates to change a position of the aperture diaphragm within the camera 104 so that the diameter of the aperture of the camera 104 is changed to be greater. The diameter is greater than a diameter of the aperture of the camera 104 when an image of the HMD 110 and the hand-held controller 108 is captured in the operation 502 (FIG. 5A) to track the HMD 110 and the hand-held controller 108. Moreover, the processor of the camera 104 sends a signal to the shutter driver within the camera 104 to provide a current signal to the drive mechanism, and the drive mechanism generates an amount of electromagnetic field, which increases a speed with which a shutter of the camera 104 is open and closed. The shutter speed is increased compared to a shutter speed used to capture the image of the HMD 110 and the hand-held controller 108 in the operation 502 (FIG. 5A). The shutter speed is increased to compensate for the greater amount of light entering the camera 104 as a result of the increased diameter of the aperture of the camera 104. The diameter of the aperture and the speed of the shutter are changed in the operation 514 to focus on a face of spectator 212 more compared to an amount of focus on the HMD 110 and the hand-held controller 108 to capture an image of the face of the spectator 212. In some embodiments, the diameter of the aperture and the speed of the shutter are changed in the operation 514 to focus on the face of spectator 212 instead of focusing on the HMD 110 and the hand-held controller 108 to capture an image of the face of the spectator 212. The image captured by the camera 104 with the increased amount of focus on the face of the spectator 212 is sent from the processor of the camera 104 via the communication medium 114 to the processor of the computing device 136. The processor of the computing device 136 determines whether the image of the face of the spectator 212 matches the pre-stored image, e.g., an image of the face, etc., in the user ID database. Moreover, upon determining that the image of the face of the spectator 212 matches the pre-stored image in the user ID database, the processor of the computing device 136 accesses the user ID of the spectator 212 and determines that the spectator 212 is identifiable. On the other hand, upon determining that the image of the face of the spectator 212 does not match the pre-stored image in the user ID database, the processor of the computing device 136 determines that the spectator 212 is unidentifiable.

As another example, the image of the face of the spectator 212 and the voice data of the spectator 212 are used to determine whether the spectator 212 is identifiable. For example, upon determining that the parameter associated with the voice data generated from the audio of the spectator 212 matches the pre-stored parameter in the user ID database and/or upon determining that the captured image of the face of the spectator 212 matches the pre-stored image in the user ID database, the processor of the computing device 136 accesses the user ID of the spectator 212 and determines that the spectator 212 is identifiable. On the other hand, upon determining that the parameter associated with the voice data does not match the pre-stored parameter in the user ID database and the captured image of the face of the spectator 212 does not match the pre-stored image in the user ID database, the processor of the computing device 136 determines that the spectator 212 is unidentifiable.

Upon determining that the spectator 212 is not identifiable in the operation 514, an operation 516 of the method 500 is performed. In the operation 516, the processor of the computing device 136 sends an instruction to the processor of the HMD 110 via the communication medium 112 (FIG. 1A) to provide a notification on the one or more display screens of the HMD 110 and/or via a sound emitter of the HMD 110. Upon receiving the instruction, the processor of the HMD 110 provides the notification. For example, the notification includes a display of a message that the spectator 212 is obstructing the trackable FOV 226, and a display of a request that the user 102 identify the spectator 212. As another example, the notification includes a display of a message that a quality factor of display of the video game is reduced as a result of the spectator 212 obstructing the trackable FOV 226. As still another example, the processor of the HMD 110 displays a face of the spectator 212 requesting the user 102 to identify the spectator 212 and also displays the message that the spectator 212 is obstructing the trackable FOV 226. As yet another example, upon receiving the instruction, the processor of the HMD 110 accesses the voice data, of the spectator 212, stored in the audio memory device of the HMD 110 and controls a digital-to-analog converter of the HMD 110 to convert the voice data into electrical signals, which are in an analog form. The voice data is received from the processor of the computing device 136 via the communication medium 112 by the processor of the HMD 110 for storage in the HMD 110. The processor of the HMD 110 further controls a speaker system, which includes one or more speakers, of the HMD 110 to convert the electrical signals into sound signals to output a sound of the spectator via the speaker system. The sound is embedded in an audio request to identify the spectator 212. The audio request is generated by the processor of the HMD 110. The user 102 is notified by the sound embedded within the request to identify the spectator 212.

In various embodiments, instead of the ultrasonic sound emitter used to emit sound waves, a light emitter is used to emit light and the photodetector system is used to detect light reflected from a real-world object. An intensity of the light that is reflected with a light intensity amplitude threshold associated with the FOV 224 is used to determine whether the real-world object is within the FOV 224. Moreover, an intensity of the light that is reflected with a light intensity amplitude limit associated with the trackable FOV 226 is used to determine whether the real-world object is within the trackable FOV 226.

It should be noted that in some embodiments, the operation 514 is performed instead of the operation 506 and 508. For example, an exposure of the camera 104 is modified, as described with reference to the operation 514 of FIG. 5B, upon determining, in the operation 504 of FIG. 5A, that the spectator 212 is within the FOV 224. As another example, an exposure of the camera 104 is modified, as described with reference to the operation 514 of FIG. 5B, upon determining, in the operation 508 of FIG. 5A, that the spectator 212 is within the trackable FOV 226. In several embodiments, an exposure of the camera 104 is modified, as described with reference to the operation 514 of FIG. 5B, periodically, e.g., at pre-determined time intervals, etc., to identify the spectator 212. For example, the processor of the computing device 136 sends an instruction to the processor of the camera 104 to modify an exposure of the camera 104 to identify the spectator 212 at periodic time intervals or aperiodic time intervals, e.g., occasionally, etc.

Figure 5C:
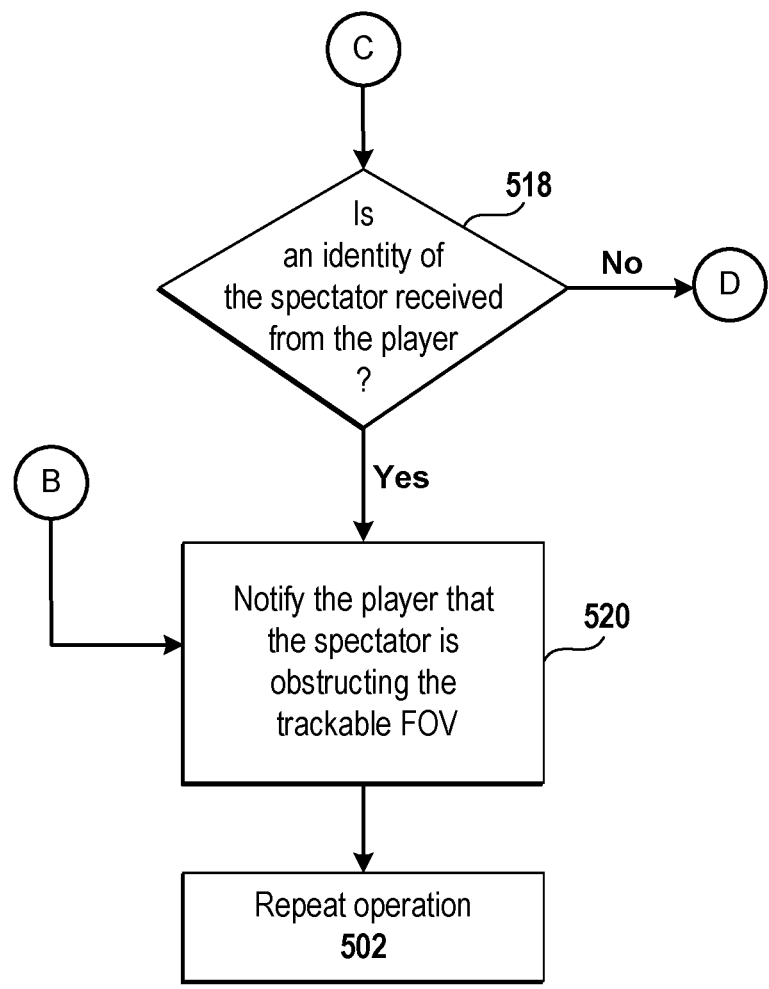
FIG. 5C is a continuation of the flowchart of the method of FIG. 5B.

FIG. 5C is a continuation of the flowchart of the method 500 of FIG. 5B. In an operation 518, it is determined whether the identity of the spectator 212 is received from the user 102. For example, the processor of the computing device 136 determines whether the user 102 provides an input, e.g., the user ID of the spectator 212, a name of the spectator 212, etc., identifying the spectator 212 via the hand-held controller 108 to the processor of the HMD 110 in response to the notification of the operation 516. To illustrate, the user 102 selects via the hand-held controller 108 various alphanumeric characters displayed on the one or more displays screens of the HMD 110 to select the name of the spectator 212. Upon receiving the input, the processor of the HMD 110 sends the input via the communication medium 112 to the processor of the computing device 136. Upon receiving the input, the processor of the computing device 136 determines that the identity of the spectator 212 is received from the user 102. In some embodiments, the processor of the HMD 110 continues to provide the notification of the operation 516 until the identity of the spectator 212 is received from the user 102.

Referring back to the operation 514 of FIG. 5B, upon determining that the spectator 212 is not identifiable, an operation 520 of the method 500 of FIG. 5C is performed. During the operation 520, the user 102 is notified that the spectator 212 is obstructing the HMD 110 and/or the hand-held controller 108 in the trackable FOV 226. For example, the processor of the computing device 136 sends an instruction to the processor of the HMD 110 via the communication medium 112 (FIG. 1A) to provide a notification on the one or more display screens of the HMD 110 and/or via the sound emitter of the HMD 110. Upon receiving the instruction, the processor of the HMD 110 provides the notification. For example, the notification includes a display of a message that the spectator 212 is obstructing the trackable FOV 226 and the message includes the user ID of the spectator 212 to identify the spectator 212 to the user 102. Moreover, the notification includes a message to the user to ask the spectator 212 to move so that the spectator 212 does not obstruct the trackable FOV 226. As another example, the processor of the HMD 110 displays the user ID of the spectator 212 and also displays the message that the spectator 212 is obstructing the trackable FOV 226. Moreover, the notification includes a message to the user 102 to ask the spectator 212 to move so that the spectator 212 does not obstruct the trackable FOV 226. As yet another example, upon receiving the instruction, the processor of the HMD 110 accesses pre-recorded voice data stored in the audio memory device of the HMD 110 and controls the digital-to-analog converter of the HMD 110 to convert the pre-recorded voice data into electrical signals, which are in an analog form. The processor of the HMD 110 further controls the speaker system of the HMD 110 to convert the electrical signals into sound signals to output a sound indicating to the user 102 that the spectator 212 having the user ID is obstructing the trackable FOV 226. As another example, upon receiving the instruction, the processor of the HMD 110 accesses pre-recorded voice data stored in the audio memory device of the HMD 110 and controls the digital-to-analog converter of the HMD 110 to convert the pre-recorded voice data into electrical signals. The processor of the HMD 110 further controls the speaker system of the HMD 110 to convert the electrical signals into sound signals to output a sound indicating to the user 102 that the spectator 212 having the user ID is obstructing the trackable FOV 226 and also requesting the spectator 212 to move so as to not obstruct the trackable FOV 226. The operation 502 is repeated after the operation 520.

In some embodiments, the spectator 212 is notified that he/she is obstructing the trackable FOV 226 via sound medium of the HMD 110. In these embodiments, between the operations 512 and 516 of FIG. 5B or between the operations 516 and 520 or between the operations 512 and 520, or between the operations 520 and 502, the processor of the computing device 136 sends an instruction to the processor of the HMD 110 via the communication medium 112 (FIG. 1A) to provide a notification via the sound emitter of the HMD 110. Upon receiving the instruction, the processor of the HMD worn by the spectator 212 provides the notification. For example, upon receiving the instruction, the processor of the HMD 110 accesses voice information stored in the audio memory device of the HMD 110 and/or received within the instruction and controls the digital-to-analog converter of the HMD 110 to convert the voice information into electrical signals, which are in an analog form. The processor of the HMD 110 further controls the speaker system of the HMD 110 to convert the electrical signals into sound signals to output a sound of the spectator 212 via the speaker system. The sound is embedded in an audio request indicating that the spectator 212 not obstruct the trackable FOV 226. The audio request is generated by the processor of the HMD 110. The spectator 212 is notified by the sound embedded within the audio request to move so as not to obstruct the trackable FOV 226.

In several embodiments, the spectator 212 is notified that he/she is obstructing the trackable FOV 226 via a display device, such as a television or a computer monitor, coupled to the computing device 136. For example, between the operations 512 and 516 of FIG. 5B or between the operations 516 and 520 or between the operations 512 and 520, or between the operations 520 and 502, the processor of the computing device 136 sends an instruction to a processor of the display device that is coupled to the computing device 136 via a communication medium, such as the wired communication medium or a wireless communication medium, to provide a notification via a display screen of the display device and/or a speaker system, such as one or more audio speakers, of the display device. An example of the wired communication medium coupling the computing device 136 to the display device is a high-definition multimedia interface (HDMI) cable. Upon receiving the instruction, the processor of the display device displays the notification. To illustrate, upon receiving the instruction, the processor of the display device displays on the display screen of the display device that the spectator 212 is obstructing the trackable FOV 226 and requests the spectator 212 to move to be outside the trackable FOV 226. As another illustration, upon receiving the instruction, the processor of the display device displays on a display screen of the display device that the spectator 212 is obstructing the trackable FOV 226 and requests the spectator 212 to move. As another illustration, upon receiving the instruction, which includes the voice information, the processor of the display device controls a digital-to-analog converter of the display device to convert the voice information into electrical signals. The processor of the display device further controls the speaker system of the display device to convert the electrical signals into sound signals to output a sound via the speaker system of the display device. The sound is embedded in an audio request indicating that the spectator 212 not obstruct the trackable FOV 226. The audio request is generated by the processor of the display device. The spectator 212 is notified by the sound embedded within the audio request to move so as not to obstruct the trackable FOV 226.

In various embodiments, the spectator 212 is also wearing an HMD on his/her head and the spectator 212 is notified via the HMD worn by the spectator 212 that the spectator 212 is obstructing the trackable FOV 226. For example, between the operations 512 and 516 of FIG. 5B or between the operations 516 and 520 or between the operations 512 and 520, or between the operations 520 and 502, the processor of the computing device 136 sends an instruction to a processor of the HMD worn by the spectator 212 via a communication medium coupled to the HMD worn by the spectator 212 to provide a notification to the spectator 212 via the HMD worn by the spectator 212. The communication medium coupled to the HMD worn by the spectator 212 is the same in structure and function as that of the communication medium 112 (FIG. 1A). Upon receiving the instruction, the processor of the HMD worn by the spectator 212 displays a notification on the HMD worn by the spectator 212 and/or generates a sound indicating the notification. To illustrate, the notification is displayed on the display screen of the display device as a message that the spectator 212 is obstructing the trackable FOV 226 and that the spectator 212 should move so as not to obstruct the trackable FOV 226. As another illustration, the notification is displayed on the display screen of the display device as a message that a quality factor of display of the video game being played by the user 102 is reduced as a result of the spectator 212 obstructing the trackable FOV 226 and that the spectator 212 should move so as not to obstruct the trackable FOV 226. As another illustration, upon receiving the instruction, which includes the voice information, the processor of the HMD worn by the spectator 212 controls a digital-to-analog converter of the HMD worn by the spectator 212 to convert the voice information into electrical signals. The processor of the HMD worn by the spectator 212 further controls the speaker system of the HMD worn by the spectator 212 to convert the electrical signals into sound signals to output a sound via a speaker system, such as one or more audio speakers, of the HMD worn by the spectator 212. The sound is embedded in an audio request indicating that the spectator 212 not obstruct the trackable FOV 226. The audio request is generated by the processor of the HMD worn by the spectator 212. The spectator 212 is notified by the sound embedded within the request to move so as not to obstruct the trackable FOV 226.

In some embodiments, the method 500 is executed by one or more processors of the cloud computing network instead of or in addition to the processor of the computing device 136. The one or more processors of the cloud computing network are coupled to the HMD 110 (FIG. 1A), the HMD 132 (FIG. 1B), or the HMD 152 (FIG. 1C) via the router.

It should be noted that although some of the embodiments, of FIGS. 5A through 5C, are described above with respect to an HMD, the embodiments apply equally as well to a hand-held controller, described herein.

Figure 6A:
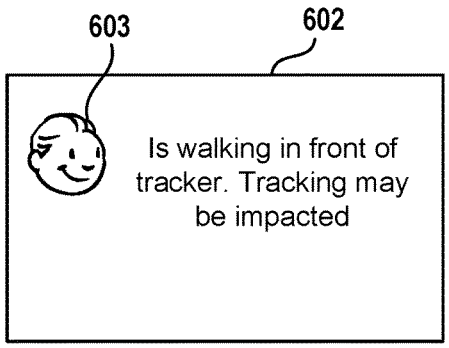
FIG. 6A is a diagram of an embodiment of a notification that is displayed on one or more screens of an HMD.

FIG. 6A is a diagram of an embodiment of a notification 602 that is displayed on the one or more screens of an HMD, e.g., the HMD 110 (FIG. 1A), or the HMD 132 (FIG. 1B), or the HMD 152 (FIG. 1C), etc. The notification 602 has an image 603 of the face of the spectator 212 and indicates to the user 102 that the spectator 212 is walking in front of a trackable FOV, e.g., the trackable FOV 226, etc., of a tracker, e.g., the camera 104 (FIG. 1A), or the projectors 138A and 138B (FIG. 1B), or the camera 202 (FIG. 2A), etc., and that tracking may be impacted.

Figure 6B:
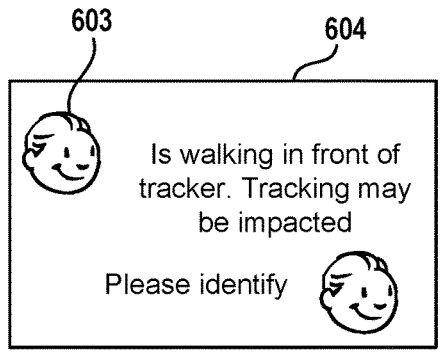
FIG. 6B is a diagram of an embodiment of another notification that is displayed on the one or more screens of an HMD.

FIG. 6B is a diagram of an embodiment of another notification 604 that is displayed on the one or more screens of an HMD, e.g., the HMD 110 (FIG. 1A), or the HMD 132 (FIG. 1B), or the HMD 152 (FIG. 1C), etc. The notification 604 has the image 603 of the face of the spectator 212 and indicates to the user 102 that the spectator 212 is walking in front of the trackable FOV of the tracker. Moreover, the notification 604 includes a request to the user 102 to identify the spectator 212 from the image 603, which is a part of the notification.

Figure 6C:
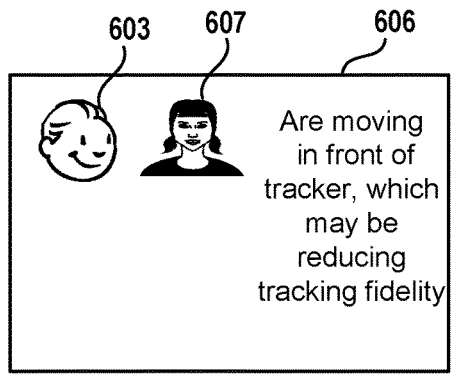
FIG. 6C is a diagram of an embodiment of a notification that is displayed on the one or more screens of an HMD.

FIG. 6C is a diagram of an embodiment of a notification 606 that is displayed on the one or more screens of an HMD, e.g., the HMD 110 (FIG. 1A), or the HMD 132 (FIG. 1B), or the HMD 152 (FIG. 1C), etc. The notification 606 has the image 603 of the face of the spectator 212 and another image 607 of a face of another spectator who is also obstructing the trackable FOV of the tracker. The notification indicates to the user 102 that the spectator 212 and the other spectator are moving in front of the trackable FOV of the tracker and the movement may reduce tracking fidelity, e.g., focus, quality, etc., of the tracker.

Figure 6D:
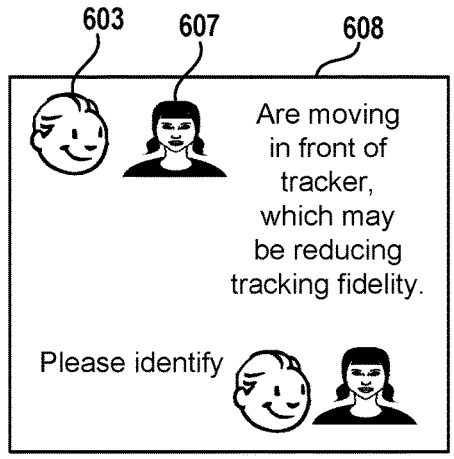
FIG. 6D is a diagram of an embodiment of another notification that is displayed on the one or more screens of an HMD.

FIG. 6D is a diagram of an embodiment of another notification 608 that is displayed on the one or more screens of an HMD, e.g., the HMD 110 (FIG. 1A), or the HMD 132 (FIG. 1B), or the HMD 152 (FIG. 1C), etc. The notification 608 has the image 603 of the face of the spectator 212 and the image 607 of the face of the other spectator, and indicates to the user 102 that the spectator 212 and the other spectator are moving in front of the trackable FOV of the tracker and the movement may reduce the tracking fidelity. Moreover, the notification includes a request to the user 102 to identify the spectator 212 from the image 603 and to identify the other spectator from the image 607, and the images 603 and 607 of the spectators are a part of the notification.

Figure 6E:
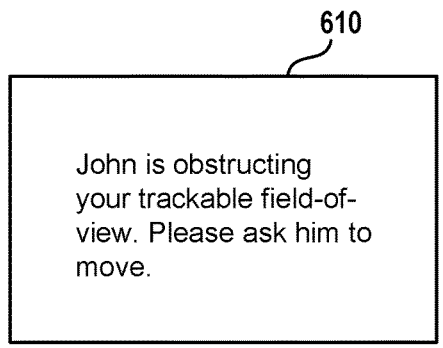
FIG. 6E is a diagram of an embodiment of a notification that is displayed on the one or more screens of an HMD.

FIG. 6E is a diagram of an embodiment of a notification 610 that is displayed on the one or more screens of an HMD, e.g., the HMD 110 (FIG. 1A), or the HMD 132 (FIG. 1B), or the HMD 152 (FIG. 1C), etc. The notification 610 has the user ID, e.g., name "John", etc., of the spectator 212 and indicates to the user 102 that the spectator 212 is obstructing a trackable FOV of the tracker. The notification 610 includes a message to the user 102 to ask John to move so that the trackable FOV of the tracker is not obstructed by John.

Figure 6F:
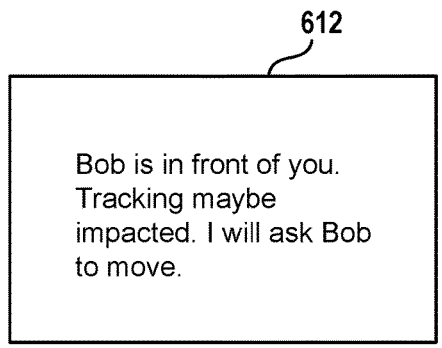
FIG. 6F is a diagram of an embodiment of a notification that is displayed on the one or more screens of an HMD.

FIG. 6F is a diagram of an embodiment of a notification 612 that is displayed on the one or more screens of an HMD, e.g., the HMD 110 (FIG. 1A), or the HMD 132 (FIG. 1B), or the HMD 152 (FIG. 1C), etc. The notification 612 has the user ID, e.g., name "Bob", etc., of the spectator 212 and indicates to the user 102 that the spectator 212 is in front of the user 102. The notification 612 further indicates to the user 102 that tracking of the tracker may be impacted. The notification 612 further includes a message to the user 102 to permit the processor of the HMD to ask Bob to move so as not to obstruct the trackable FOV of the tracker. Upon receiving an indication selection of a button of the hand-held controller 108 via the communication medium 116 (FIG. 1A), the processor of the computing device 136 sends an instruction to the processor of the HMD 110 via the communication medium 112 (FIG. 1A). Upon receiving the instruction, the processor of the HMD 110 commands the sound emitter to emit a sound to request Bob to move to not obstruct the trackable FOV of the tracker.

Figure 6G:
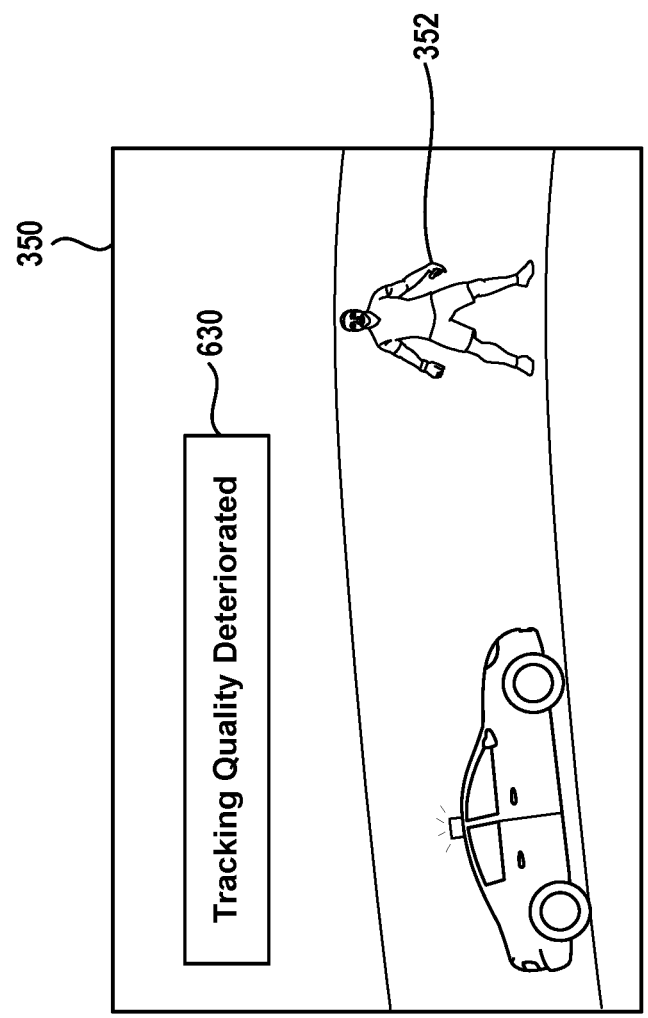
FIG. 6G is a diagram of an embodiment of an image displayed on the one or more displays screens of an HMD and the image includes a notification.

FIG. 6G is a diagram of an embodiment of the image 350 displayed on the one or more displays screens of the HMD 110 and the image 350 includes a notification 630. The notification 630 indicates that tracking quality is deteriorated when the trackable FOV of the tracker is obstructed by the spectator 212. The notification 630 is embedded within the image 350 of the video game.

Figure 7:
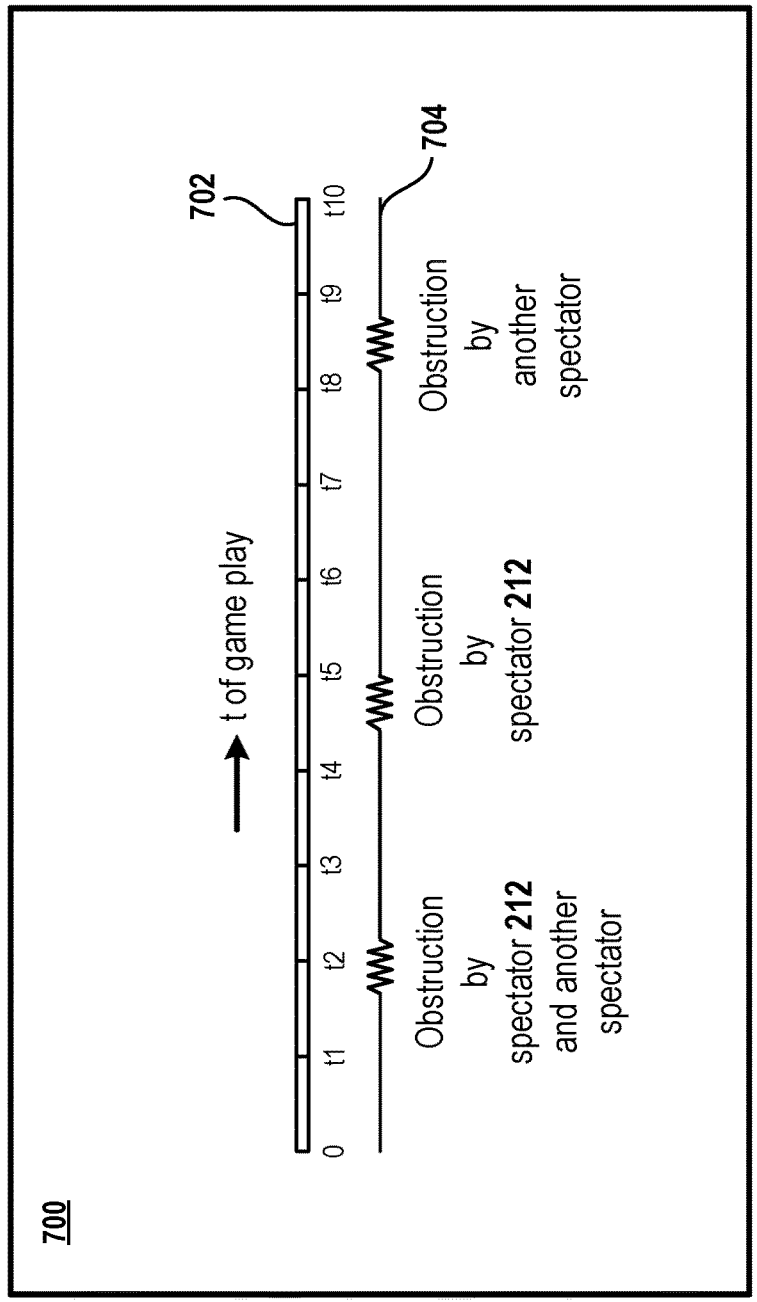
FIG. 7 is a diagram of an embodiment of an image that is displayed on the one or more display screens of an HMD.

FIG. 7 is a diagram of an embodiment of an image that is displayed on the one or more display screens of the HMD 110. The image 700 includes a timeline 702 of play of the video game by the user 102 and an obstruction indicator 704, e.g., an obstruction line, etc. The timeline 702 plots times t1, t2, t3, t4, t5, t6, t7, t8, t9, and t10 in a chronological order. Moreover, along the timeline 702, the obstruction indicator 704 showing obstruction by one or more spectators, e.g., the spectator 212 or the other spectator, or both the spectator 212 and the other spectator, etc., is plotted. For example, at the time t2, both the spectator 212 and the other spectator are obstructing the HMD 110 and/or the hand-held controller 108 in the trackable FOV 226. As another example, between times t4 and t5, the spectator 212 is obstructing the HMD 110 and/or the hand-held controller 108 in the trackable FOV 226. As yet another example, between times t8 and t9, the other spectator is obstructing the HMD 110 and/or the hand-held controller 108 in the trackable FOV 226.

The image 700 is rendered by the processor of the HMD 110 and displayed on the one or more display screens of the HMD 110. The processor of the computing device 136 determines whether the spectator 212 or the other spectator, or both the spectator 212 and the other spectator are obstructing the HMD 110 and/or the hand-held controller 108 in the trackable FOV 226 and determines user IDs of both the spectators. Moreover, at a time, it is determined that a spectator is obstructing the HMD 110 and/or the hand-held controller 108 in the trackable FOV 226, the time is recorded by the processor of the memory device of the computing device 136. As an example, the time is obtained by the processor of the computing device 136 from a computer network, e.g., the Internet, or an Intranet, or a local area network, or a wide area network, or a combination thereof, etc., or the cloud computing network. For example, the processor of the computing device 136 synchronizes a clock of its operating system with that of a network time protocol (NTP) server, which is accessed by the processor of the computing device 136 via the computer network. The processor of the computing device 136 generates image data for the image 700 including timeline data for the timeline 702 and data for the obstruction indicator 704. For example, the obstruction indicator 704 includes multiple waves, e.g., sawtooth waves, etc., that indicate an obstruction by a spectator at a time of the obstruction, e.g., at a time the processor of the computing device 136 determines that a spectator is obstructing the trackable FOV of the tracker, etc. In addition, the image data generated by the processor of the computing device 136 includes user ID data to indicate along the obstruction indicator 704 a user ID of a spectator who is obstructing the trackable FOV of the tracker.

The processor of the computing device 136 sends the image data for the image 700 via the communication medium 112 (FIG. 1A) to the processor of the HMD 110. The processor of the HMD 110 renders the image data for generating the image 700 on the one or more display screens of the HMD 110 for view by the user 102.

In some embodiments, the processor of the computing device 136 determines to award a user account of the user 102 with extra credits upon determining that during game play of the video game the trackable FOV, e.g., the HMD 110 and/or the hand-held controller 108 in the trackable FOV 226, etc., of the tracker was obstructed. For example, in a multi-player game, the processor of the computing device 136 determines that the user 102 has the obstructed trackable FOV but another user, e.g., another player of the video game, etc., does not have the obstructed trackable FOV. Upon determining so, the processor of the computing device 136 awards the extra credits, e.g., extra game points, extra time for play, etc., to the user 102 compared to the other user. To illustrate, when both the users, e.g., the user 102 and the other user, etc., are allotted an x time period to play the video game, upon determining that the trackable FOV of the tracker that is tracking movement of the HMD 900 worn by the user 102 is obstructed and another trackable FOV of another tracker that is tracking movement of the HMD 900 worn by the other user is not obstructed, the processor of the computing device 136 allocates an x+y time period to the user 102 but allocates the x time period to the other user to play the video game.

FIG. 8A is an embodiment of a graph 800 to illustrate a change in a frame rate at which consecutive images of the video game are displayed on the one or more display screens of an HMD, e.g., the HMD 110 (FIG. 1A), or the HMD 132 (FIG. 1B), or the HMD 152 (FIG. 1C), etc. The graph 800 plots the frame rate, measured in frames per second (FPS), versus time t. The graph 800 has a plot 802 that plots the frame rate from a time the spectator 212 is walking by the user 102 and within the trackable FOV of the tracker but not obstructing the trackable FOV to a time the spectator 212 is obstructing the trackable FOV and further to a time the spectator 212 is no longer obstructing the trackable FOV. During a time period in which the spectator 212 is in the trackable FOV without obstructing the trackable FOV, the frame rate is a normal frame rate, e.g., 30 frames per second, 60 frames per second, etc. For example, until a time tx, the processor of the HMD 110 displays images of the video game at the normal frame rate on the one or more display screens of the HMD 110. When there is no obstruction of the trackable FOV, states of the video game are generated by the processor of the computing device 136 based on images of the HMD 110 and of the hand-held controller 108 captured by the camera 104 (FIG. 1A). The states are generated based on a movement of the HMD 110, or based on movement of the hand-held controller 108, or a combination thereof. For example, an angle of a view of an image of the video game is changed when the HMD 110 is moved by the user 102. Video game data implementing the states of the video game is sent from the processor of the computing device 136 via the communication medium 112 to the processor of the HMD 110. Examples of the video game data include a color, a texture, and a shade of a virtual object in the video game, and a color, a texture, and a shade of the background in the video game, etc. The processor of the HMD 110 renders the video game data to display images of the video game on the one or more display screens of the HMD 110 at the normal frame rate.

On the other hand, when the trackable FOV is obstructed by the spectator 212 during a time period, e.g., between the time tx and a time ty, the states of the video game are generated at a lower speed by the processor of the computing device 136 based on movement of the HMD 110, or based on movement of the hand-held controller 108, or a combination thereof. The lower speed is lower than a speed of generation of the states for achieving the normal frame rate. At least a portion of the HMD 110 and/or at least a portion of the hand-held controller 108 is not detected to the tracker when the trackable FOV is obstructed by the spectator 212. For example, the camera 104 cannot focus on the HMD 110 and/or the hand-held controller 108. As another example, the camera 104 cannot focus on at least one of the markers 412A through 412E of the HMD 110. As yet another example, the camera 104 is not able to capture an image of at least one of the markers 412A through 412E. As yet another example, the camera 104 is not able to capture an image of at least one of the markers 426A and 426B of the hand-held controller 108. When the game states are generated at the lower speed, the processor of the computing device 136 transfers the video game data via the communication medium 112 to the processor of the HMD 110. The processor of the HMD 110 receives the video game data and generates images at a frame rate, e.g., 5 frames per second, etc., than is lower than the normal frame rate. Such lower frame rate results in a less than optimal video gaming experience by the user 102 while playing the video game. In some embodiments, a frame rate or a speed with which the states are generated is an example of the quality factor. In various embodiments, a speed with which the position and orientation of the HMD 110 and/or the hand-held controller 108 is determined is an example of the quality factor.

Figure 8B:
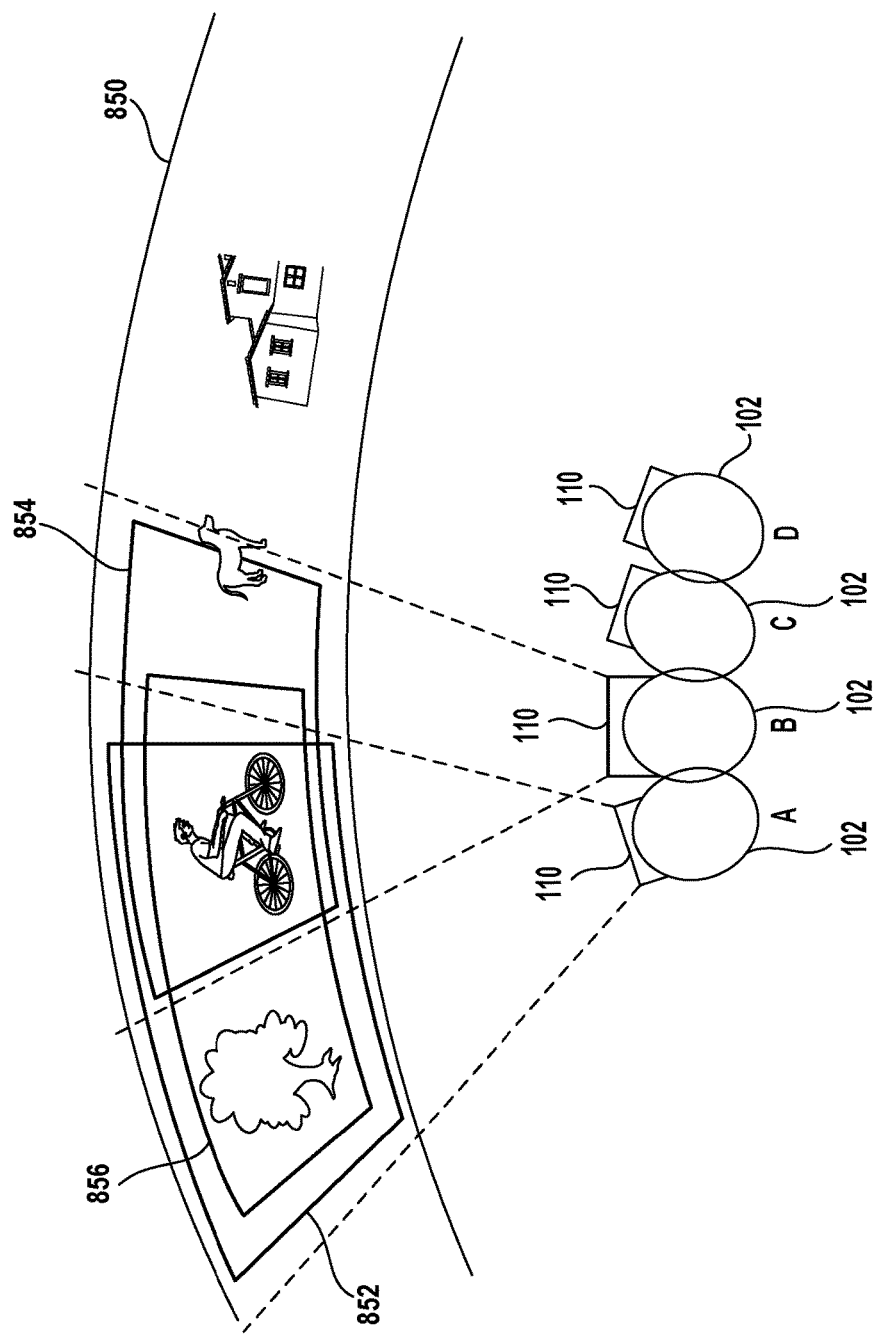
FIG. 8B is a diagram of an embodiment of a scene that is viewed via an HMD to illustrate a jump in the scene as a result of an obstruction by a spectator.

FIG. 8B is a diagram of an embodiment of a scene 850 that is viewed via the HMD 110 to illustrate a jump in the scene 850 as a result of an obstruction by the spectator 212. When the HMD 110 is at a position A, a portion 852 of the scene 850 is displayed on the HMD 110 to the user 102. When the HMD 110 moves from the position A to a position B while transitioning to a position C and further to a position D, and when the trackable FOV is being obstructed by the spectator 212, a portion 854 of the scene 850 is displayed on the HMD 110. The portion 854 is displayed immediately after the portion 852 is displayed. This is because the position and orientation of the HMD 110 corresponding to the display of a portion 856 cannot be determined as a result of the obstruction. When the trackable FOV is not being obstructed by the spectator 212, a portion 856 of the scene 850 is displayed on the HMD 110 after the portion 852 is displayed, and after the portion 856 is displayed, the portion 854 is displayed on the HMD 110. There is a jump from the portion 852 to the portion 854 when the spectator 212 obstructs the trackable FOV. Another example of the quality factor, as described herein, is an order of display of portions of the scene 850. When one of the portions of the scene 850 between two portions of the scene 850 is not displayed on the HMD 110, there is a reduction in the quality factor.

The user 102 is immersed in the scene 850, and does not know why there is a change in the quality factor. The user 102 does not know what happens in the real-world after being immersed. The processor of the computing device 136 identifies that the change in the quality factor is as a result of the obstruction by the spectator 212 and notifies the user 102 of the same.

Figure 9:
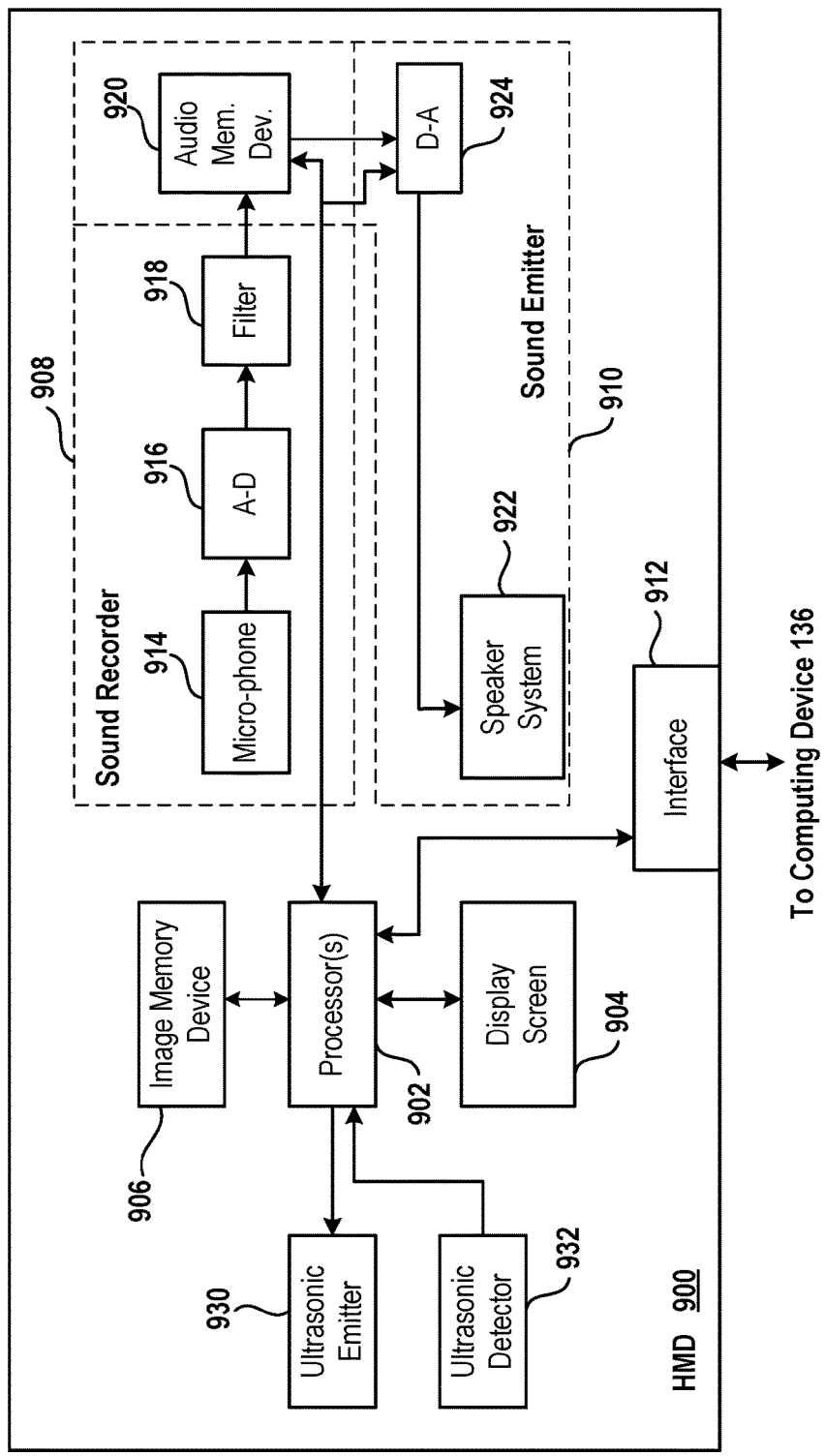
FIG. 9 is a diagram of an embodiment of an HMD.

FIG. 9 is a diagram of an embodiment of an HMD 900, which is an example of the HMD 110 (FIG. 1A), or the HMD 132 (FIG. 1B), or the HMD 152 (FIG. 1C). The HMD 900 includes a processor 902, a display screen 904, an image memory device 906, a sound recorder 908, a sound emitter 910, an interface 912, an ultrasonic emitter 930, and an ultrasonic detector 932. As used herein, a processor is a central processing unit, or a microprocessor, or a microcontroller, or an application specific integrated circuit (ASIC), or a programmable logic device (PLD). Moreover, as used herein, a memory device is a read-only memory (ROM), or a random access memory (RAM), or a device that include both RAM and ROM. Examples of a memory device include a flash memory, a redundant array of independent disks (RAID), a hard disk, etc. Example of a display screen, as used herein, include a liquid crystal display (LCD) screen, a light emitting diode (LED) display screen, a plasma display screen, etc. Examples of an interface, as used herein, include a parallel interface for a parallel transfer of data, a universal serial bus (USB) interface, a circuit for implementing a wireless transfer protocol, e.g., Bluetooth™, Wi-Fi™, RF, etc. for communication via a wireless medium, etc. The sound recorder 908 includes a microphone 914, an analog-to-digital converter 916, a filter 918, and an audio memory device 920. Moreover, the sound emitter 910 includes the audio memory device 920 and a speaker system 922, which includes one or more speakers.

The processor 902 accesses image data stored in the image memory device 906 and renders the image data to display images, e.g., images of the video game, images of a notification, an image of a notification embedded within an image of the video game, etc., onto the display screen 904. The image data is of the video game or of a notification. The image data is received from the processor of the computing device 136 via the communication medium 112 (FIG. 1A) and the interface 912.

Moreover, the processor 902 sends a signal, e.g., an enable signal, etc., to the microphone 914 to enable the microphone 914 to collect a sound of the spectator 212 and convert the sound into electrical signals. The electrical signals are then converted by the analog-to-digital converter 916 from an analog format to a digital format to generate data. The data is filtered by the filter 912 to remove noise from the data to generate filtered data. The filtered data is stored in the audio memory device 920. In some embodiments, the processor 902 accesses the filtered data from the audio memory device 920 and sends the filtered data via the interface 912 to the processor of the computing device 136 for comparing the filtered data with voice data that is pre-stored in the memory device of the computing device 136.

The processor 902 receives audio data from the processor of the computing device 136 via the communication medium 112 and the interface 912 and stores the audio data in the audio memory device 920. Examples of the audio data received from the processor of the computing device 136 include a notification to the spectator 212 to move so that the trackable FOV is not obstructed.

The processor 920 accesses the filtered data and/or the audio data stored in the audio memory device 920 and provides the filtered data and/or the audio data to the digital-to-analog converter 924. The digital-to-analog converter 924 converts the filtered data and/or the audio data from the digital format to an analog format to generate electrical signals. The speaker system 922 converts the electrical signals into sound and outputs the sound into the real-world environment 220 (FIG. 2B).

The processor 920 sends a signal to the ultrasonic emitter 930. Upon receiving the signal, the ultrasonic emitter 930 emits ultrasonic waves towards a real-world environment, described herein. Ultrasonic waves that are reflected from the real-world environment are detected by the ultrasonic detector 932 to generate electrical signals. The electrical signals are sent from the ultrasonic detector 932 to the processor 902 after being converted from an analog format to a digital format. The processor 902 receives data, which is the digital formatted electrical signals, and sends the data via the interface 912 to the processor of the computing device 136 for determining a distance between a real-world object, e.g., the HMD 110, the spectator 212, the hand-held controller 108, etc., of a real-world environment, described herein, and the tracker.

In some embodiments, instead of the processor 902, any other number of processors is used to execute functions, described herein, as being performed by the processor 902.

In various embodiments, the sound recorder 908 excludes the filter 918 and the analog-to-digital converter 916 is connected to the audio memory device 920.

Figure 10:
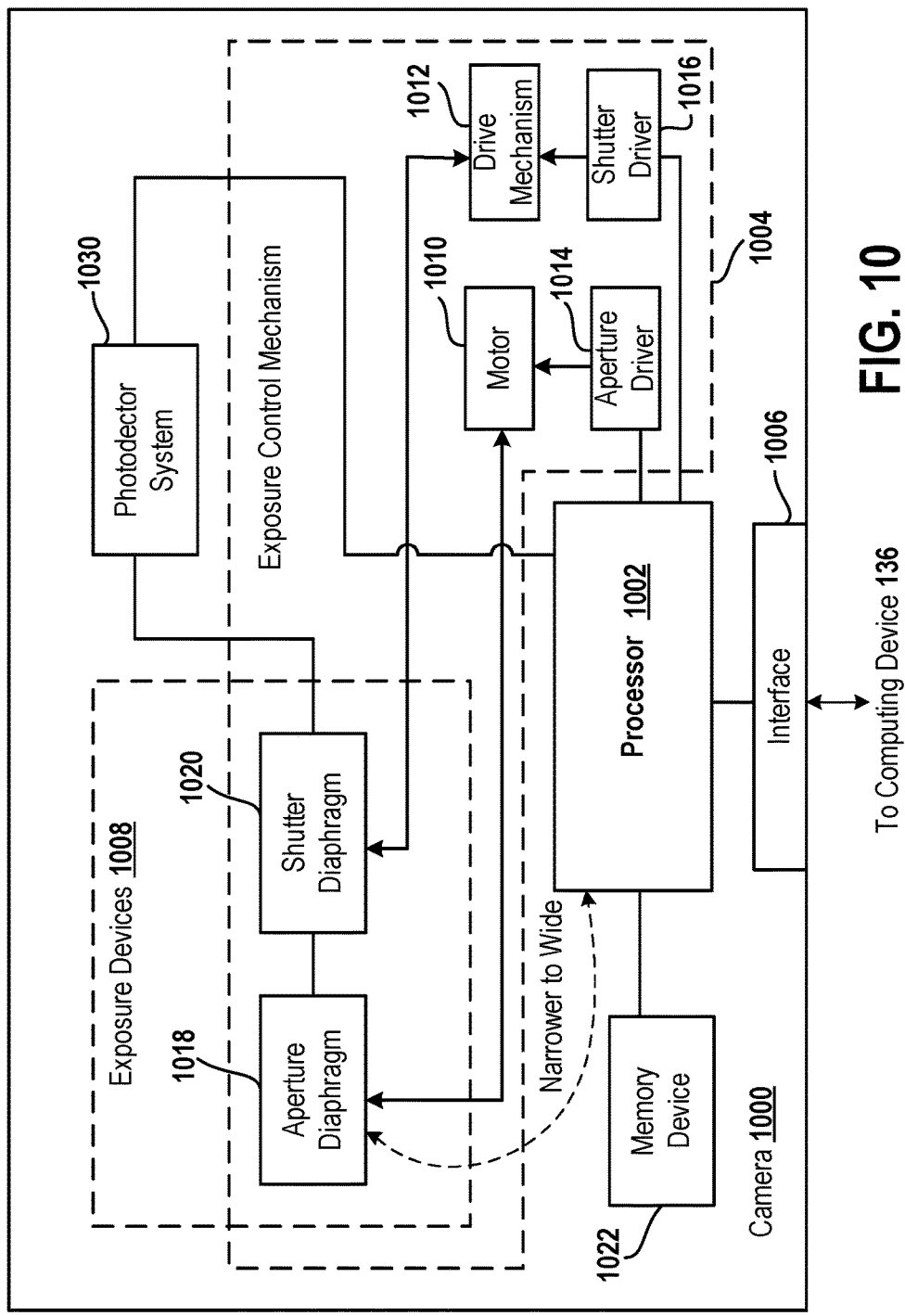
FIG. 10 is a diagram of an embodiment of a camera.

FIG. 10 is a diagram of an embodiment of a camera 1000, which is an example of the camera 104 (FIG. 1A) or the camera 202 (FIG. 2A) of the HMD 152 (FIG. 2A). The camera 1000 includes a processor 1002, an exposure control mechanism 1004, an interface 1006, a memory device 1022, and a photodetector system 1030, which includes multiple photosensors for detecting light reflected from a real-world environment, described herein. The exposure control mechanism 1004 includes exposure devices 1008, a motor 1010, a drive mechanism 1012, an aperture driver 1014, and a shutter driver 1016. An example of the aperture driver 1014 include one or more transistors. An example of the shutter driver 1016 include one or more transistors. Moreover, an example of the motor 1010 includes a stepper motor. An example of the drive mechanism 1012 includes a coil. The exposure device 1008 includes an aperture diaphragm 1018 and a shutter diaphragm 1020.

The processor 1002 receives an instruction from the processor of the computing device 136 via the interface 1006 to change exposure, e.g., increase a size of an aperture formed between the aperture diaphragm 1018, decrease a size of the aperture, increase a speed of opening and closing of the shutter diaphragm 1020, decrease the speed, etc., of the camera 1000. The processor 1002 upon receiving the instruction sends a signal to the aperture driver 1014. The aperture driver 1014, upon receiving the signal, generates a current signal to send to the motor 1010. The motor 1010, upon receiving the current signal, rotates to change a diameter of the aperture of the aperture diaphragm 1018 to further change a depth of focus of the camera 1000. For example, for a narrow aperture, e.g., aperture with a smaller diameter, etc., the depth of focus is greater than for a broader aperture, e.g., aperture with a larger diameter, etc. Moreover, upon receiving the instruction, the processor 1002 generates another signal and sends the other signal to the shutter driver 1016. Upon receiving the other signal, the shutter driver 1016 generates an amount of a current signal and sends the current signal to the drive mechanism 1012. The drive mechanism 1012 upon receiving the current signal generates an amount of an electromagnetic field to open and close the shutter diaphragm at a speed to control an amount of light that is detected by the photodetector system 1030 of the camera 1000.

Moreover, any images that are captured by the photodetector system 1030 are stored by the processor 1002 in the memory device 1002. The images are accessed by the processor 1002 from the memory device 1002 and sent via the interface 1006 to the processor of the computing device 136.

Figure 11:
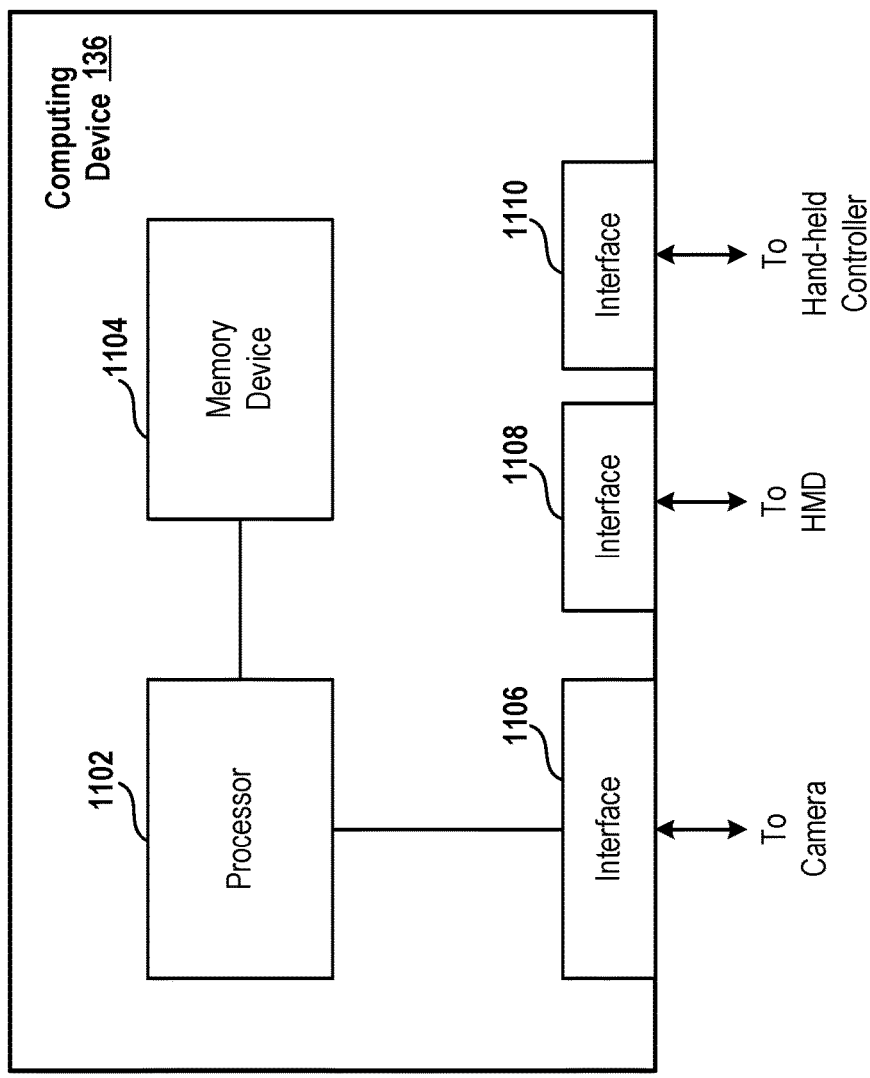
FIG. 11 is a diagram of an embodiment of a computing device.

FIG. 11 is a diagram of an embodiment of the computing device 136. The computing device 136 includes a processor 1102, a memory device 1104, an interface 1106, an interface 1108, and an interface 1110. Various functions of the processor 1102 and the memory device 1104 are described herein. Moreover, the processor 1102 communicates with the processor 1002 of the camera 1000 (FIG. 10) via the interface 1106. The processor 1102 communicates with the processor 902 of the HMD 900 via the interface 1108, and the processor 1102 communicates with a hand-held controller, e.g., the hand-held controller 108 (FIG. 1A), the hand-held controller 134 (FIG. 1B), or the hand-held controller 154 (FIG. 1C), etc., via the interface 1110.

Figure 12:
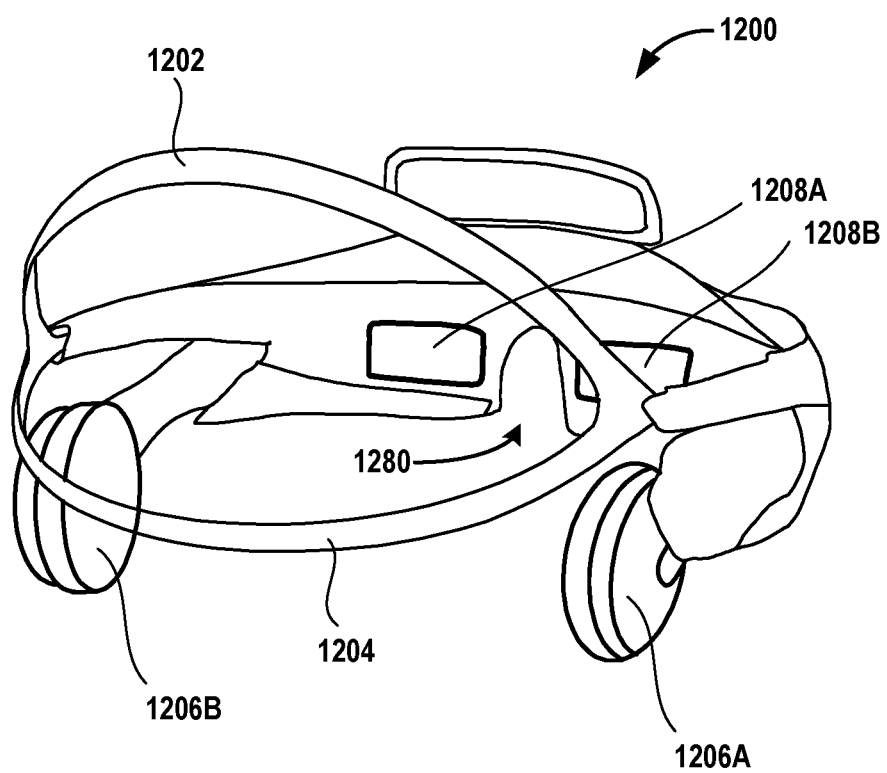
FIG. 12 is an isometric view of an HMD.

FIG. 12 is an isometric view of an HMD 1200, which is an example of the HMD 110 (FIG. 1A), or the HMD 152 (FIG. 1C). The HMD 1200 includes bands 1202 and 1204 that go to the back of the head of the user when worn by the user 102. Moreover, the HMD 1200 includes earphones 1206A and 1206B, e.g., speakers, etc., that emanate sound associated with a virtual environment, e.g., a game environment, a virtual tour environment, etc., that is generated by execution of a computer program, e.g., the game code of the video game, a game program, a virtual environment generation program, etc. The HMD 1200 includes lenses 1208A and 1208B that allows the user to view a virtual environment that is displayed on a display screen of the HMD 1200. A groove 1280 rests on a nose of the user 102 to support the HMD 1200 on the nose.

In some embodiments, the HMD 1200 is worn by the user 102 in a manner similar to which sunglasses, glasses, or reading glasses are worn by the user 102.

Figure 13:
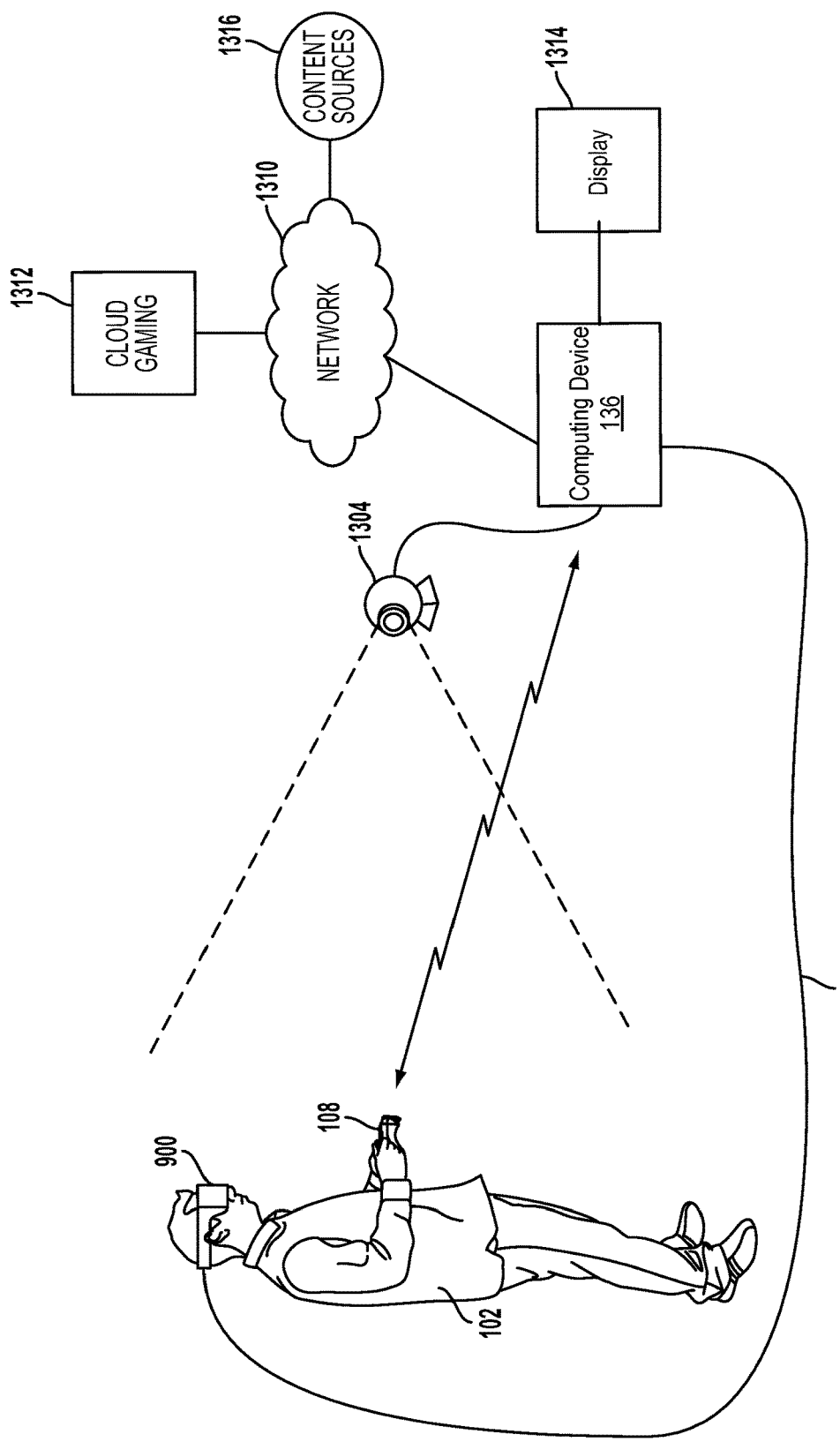
FIG. 13 illustrates a system for interactive game play of a video game, in accordance with an embodiment described in the present disclosure.

FIG. 13 illustrates a system for interactive game play of the video game, in accordance with an embodiment described in the present disclosure. The user 102 is shown wearing the HMD 900. The HMD 900 is worn in a manner similar to glasses, goggles, or a helmet, and is configured to display a video game or other content to the user 102. The HMD 900 provides an immersive experience to the user 102 by virtue of its provision of display mechanisms (e.g., optics and display screens) in close proximity to eyes of the user 102 and the format of content that is delivered to the HMD 900. In one example, the HMD 900 provides display regions to each eye of the user 102 and the display regions occupy large portions or even the entirety of a field-of-view of the user 102.

In one embodiment, the HMD 900 is connected to the computing device 136. The connection to computing device 136 is wired or wireless. The computing device 136, in one embodiment, is any general or special purpose computer, including but not limited to, a game console, a personal computer, a laptop, a tablet, a mobile device, a smart phone, a tablet, a thin client, a set-top box, a media streaming device, a smart television, etc. In some embodiments, the HMD 900 connects directly to a computer network 1310, e.g., the Internet, an Intranet, a local area network, a wide area network, etc., which allows for cloud gaming without the need for a separate local computer. In one embodiment, the computing device 136 executes the video game (and other digital content), and output the video and audio from the video game for rendering by the HMD 900. The computing device 136 is also sometimes referred to herein as a client system, which in one example is a video game console.

The computing device 136, in some embodiments, is a local or remote computer, and the computer runs emulation software. In a cloud gaming embodiment, the computing device 136 is remote and is represented by a plurality of computing services that are virtualized in data centers, where game systems/logic is virtualized and distributed to the user 102 over the computer network 1310.

The user 102 operates the hand-held controller 108 to provide input for a virtual environment. In one example, the hand-held controller 108 captures image of the environment, e.g., a real-world environment, etc., in which the user 102 is located. These captured images are analyzed to determine a location and movements of the user 102, the HMD 900, and the hand-held controller 108. In one embodiment, the hand-held controller 108 includes a light (or lights) which are tracked to determine its location and orientation. Additionally, as described in further detail below, in one embodiment, the HMD 900 includes one or more lights, which are tracked as markers to determine the location and orientation of the HMD 900 in substantial real-time during a display of a virtual environment.

The hand-held controller 108, in one embodiment, includes one or more microphones to capture sound from the real-world environment. Sound captured by a microphone array is processed to identify a location of a sound source. Sound from an identified location is selectively utilized or processed to exclusion of other sounds not from the identified location. Furthermore, in one embodiment, the hand-held controller 108 or the HMD 900 includes multiple image capture devices (e.g. stereoscopic pair of cameras), an infrared (IR) camera, a depth camera, and combinations thereof.

In some embodiments, the computing device 136 executes games locally on processing hardware of the computing device 136. The games or content is obtained in any form, such as physical media form (e.g., digital discs, tapes, cards, thumb drives, solid state chips or cards, etc.) or by way of download from the computer network 1310.

In an embodiment, the computing device 136 functions as a client in communication over the computer network 1310 with a cloud gaming provider 1312. The cloud gaming provider 1312 maintains and executes the video game being played by the user 102. The computing device 136 transmits inputs from the HMD 900 and the hand-held controller 108 to the cloud gaming provider 1312, which processes the inputs to affect the game state of the video game being executed. The output from the executing video game, such as video data, audio data, and haptic feedback data, is transmitted to the computing device 136. The computing device 136 further processes the data before transmission or directly transmits the data to the relevant devices. For example, video and audio streams are provided to the HMD 900, whereas a vibration feedback command is provided to the hand-held controller 108.

In one embodiment, the HMD 900 and the hand-held controller 108 are networked devices that connect to the computer network 1310 to communicate with the cloud gaming provider 1312. For example, the computing device 136 is a local network device, such as a router, that does not otherwise perform video game processing, but facilitates passage of network traffic. The connections to the computer network 1310 by the HMD 900 and the hand-held controller 108 are wired or wireless.

In some embodiments, content executed on the HMD 900 or displayable on a display device 1314, is obtained from any of content sources 1316. Example content sources can include, for instance, internet websites that provide downloadable content and/or streaming content. In some examples, the content can include any type of multimedia content, such as movies, games, static/dynamic content, pictures, social media content, social media websites, virtual tour content, cartoon content, etc.

In one embodiment, the user 102 is playing the video game on the HMD 900, where such content is immersive three-dimensional (3D) interactive content. The content on the HMD 900, while the user 102 is playing, is shared to the display device 1314. In one embodiment, the content shared to the display device 1314 allows other users proximate to the user 102 or remote to watch along with game play of the user 102. In still further embodiments, another player viewing the game play of the user 102 on the display device 1314 participates interactively with user 102. For example, another user viewing the game play on the display device 1314 controls characters in the game scene, provides feedback, provides social interaction, and/or provides comments (via text, via voice, via actions, via gestures, etc.,) which enables the other user who is not wearing the HMD 900 to socially interact with the user 102.

Figure 14:
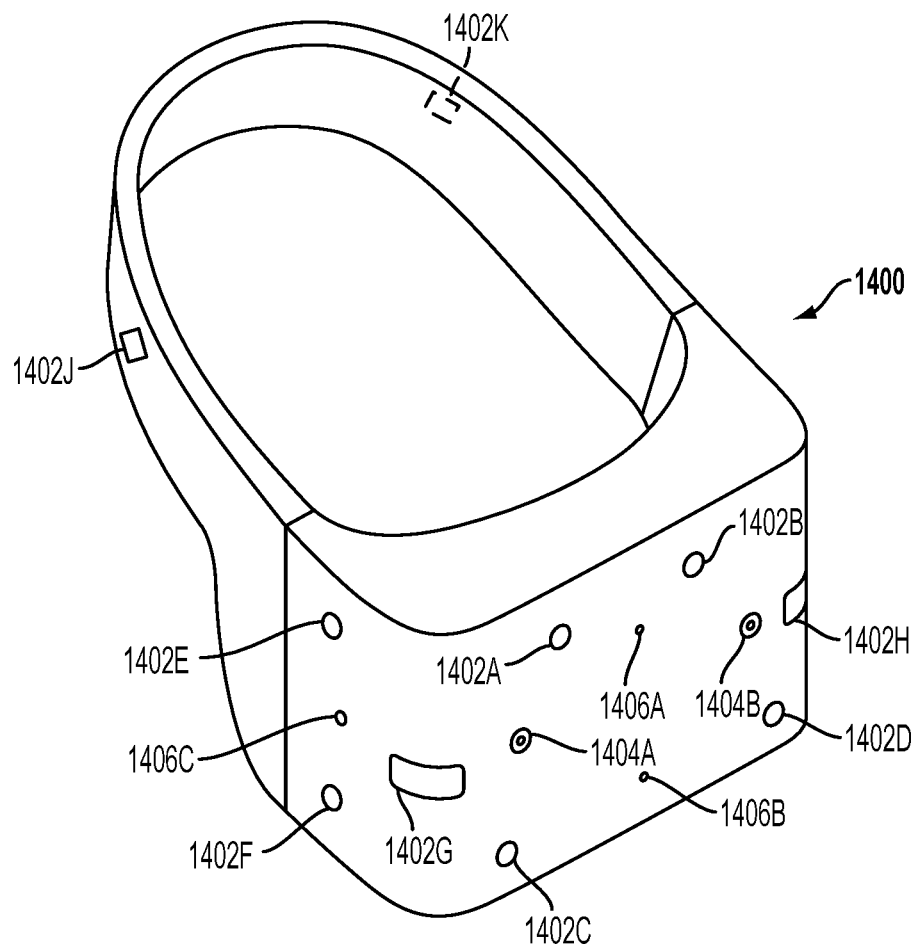
FIG. 14 illustrates an HMD, in accordance with an embodiment described in the present disclosure.

FIG. 14 illustrates an HMD 1400, in accordance with an embodiment described in the present disclosure. The HMD 1400 is an example of the HMD 132 (FIG. 1B). As shown, the HMD 1400 includes a plurality of photosensors 1402A-H, J and K (e.g., where 1402K and 1402J are located toward the rear or backside of the HMD headband). Each of these photosensors are configured to have specific shapes and/or positions. The photosensors 1402A, 1402B, 1402C, and 1402D are arranged on the front surface, e.g., front face, etc., of the HMD 1400. The photosensors 1402E and 1402F are arranged on a side surface of the HMD 1400. And the photosensors 1402G and 1402H are arranged at corners of the HMD 1400, so as to span the front surface and a side surface of the HMD 900.

Based on one or more of laser beams detected by one or more of the photosensors 1402A-H, J and K, a location of the HMD 1400 in a real-world environment is determined. It will further be appreciated that some of the photosensors cannot detect a beam depending upon the particular orientation of the HMD 1400 relative to one of the projectors 138A and 138B (FIG. 1B). In some embodiments, inertial sensors are disposed in the HMD 1400, which provide feedback regarding positioning instead of the photosensors 1302A-H, J and K. In some embodiments, the photosensors 1302A-H, J and K and inertial sensors work together, to enable mixing and selection of position/motion data.

The HMD 1400, in one embodiment, additionally includes one or more microphones. In the illustrated embodiment, the HMD 1400 includes microphones 1404A and 1404B located on the front surface of the HMD 1400, and a microphone located on a side surface of the HMD 1400. By utilizing an array of microphones, sound from each of the microphones is processed to determine a location of the sound's source. This information is utilized in various ways, including exclusion of unwanted sound sources, association of a sound source with a visual identification, etc.

In an embodiment, the HMD 1400 includes one or more image capture devices. In the illustrated embodiment, the HMD 1400 is shown to include image capturing devices 1406A and 1406B. In an embodiment, by utilizing a stereoscopic pair of image capture devices, 3D images and video of the real-world environment is captured from the perspective of the HMD 1400. Such video is presented to the user 102 to provide the user 102 with a "video see-through" ability while wearing the HMD 1400. That is, though the user 102 cannot see through the HMD 1400 in a strict sense, the video captured by the image capture devices 1406A and 1406B nonetheless provides a functional equivalent of being able to see the real-world environment external to the HMD 1400 as if looking through the HMD 1400.

Such video, in one embodiment, is augmented with virtual elements to provide an augmented reality experience, or is combined or blended with virtual elements in other ways. Though in the illustrated embodiment, two cameras are shown on the front surface of the HMD 1400, it will be appreciated that there may be any number of externally facing cameras or a single camera can be installed on the HMD 1400, and oriented in any direction. For example, in another embodiment, there may be cameras mounted on the sides of the HMD 1400 to provide additional panoramic image capture of the environment.

Figure 15:
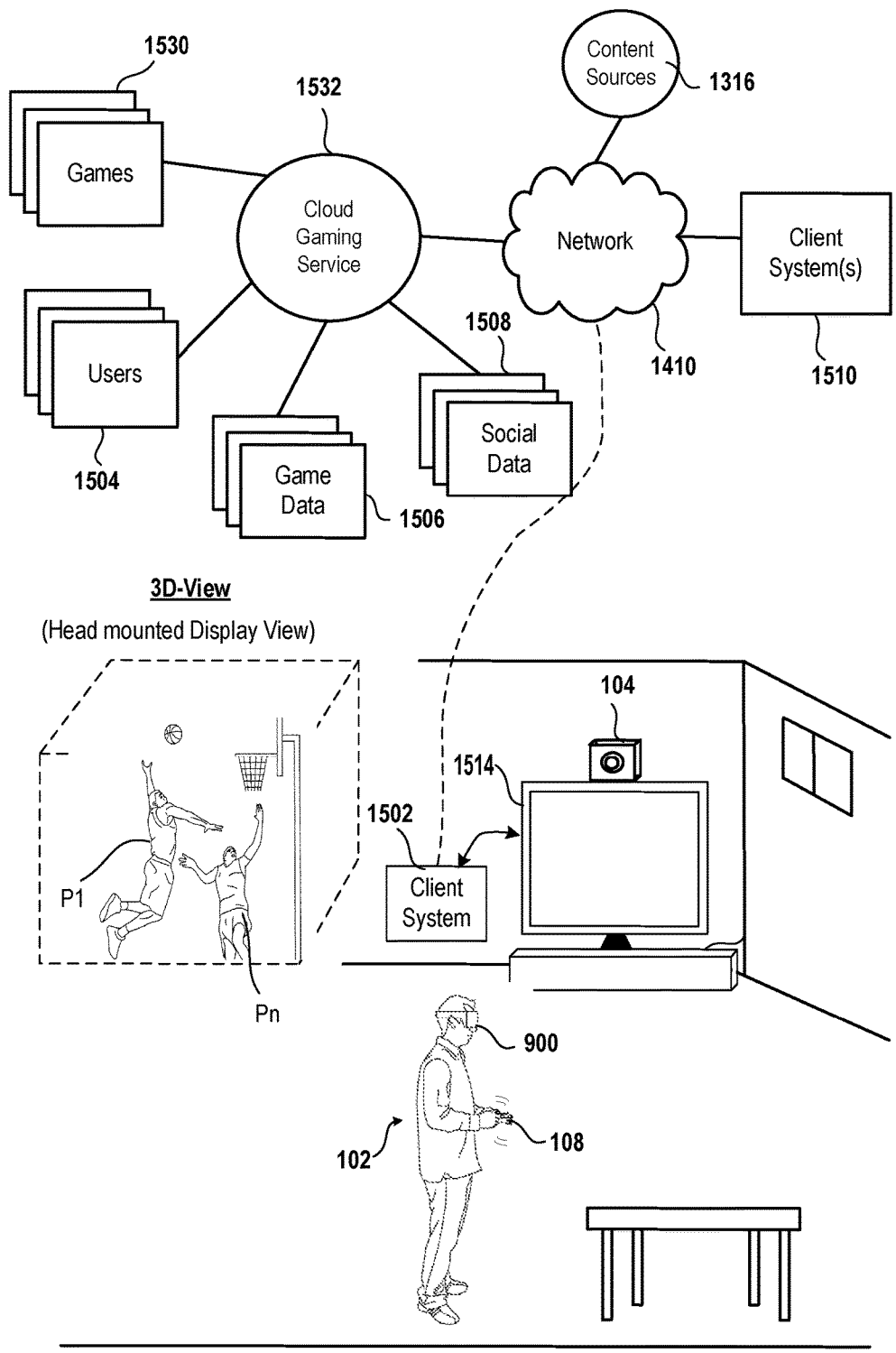
FIG. 15 illustrates one example of game play using a client system that is capable of rendering the video game content to an HMD operated by the user.

FIG. 15 illustrates one example of game play using a client system 1502 that is capable of rendering the video game content to the HMD 900 operated by the user 102. In this illustration, a state of a virtual object, e.g., game content, etc., provided to the HMD 900 is in a rich interactive 3D space. As discussed above, a state of a virtual object is downloaded to the client system 1502 or is executed in one embodiment by a cloud processing system. A cloud gaming service 1532 includes a database 1504 of user accounts of users, who are allowed to access particular games 1530, share experiences with other friends, post comments, and manage their account information.

The cloud gaming service 1532 stores game data 1506 for specific user accounts, which may be usable during game play, future game play, sharing to a social media network, or used for storing trophies, awards, status, ranking, etc. Social data 1508 is managed by the cloud gaming service 1532. In one embodiment, the social data 1508 is managed by a separate social media network, which is interfaced with cloud gaming service 1532 over the computer network 1310. Over the computer network 1310, any number of client systems 1510 are connected for access to the content and interaction with other users.

Continuing with the example of FIG. 15, the 3D interactive scene viewed in the HMD 900 includes game play, such as the characters illustrated in the 3D view, or another virtual environment. One character, e.g. P1, etc., is controlled by the user 102, who is wearing the HMD 900. This example shows a basketball scene between two players, wherein the user 102 is dunking a ball on another character in the 3-D view. The other character can be an AI (artificial intelligence) character of the game, or can be controlled by another player or players (Pn). The user 102, who is wearing the HMD 900, is shown moving about in a space of use, where the HMD 900 moves around based on head movements and body positions of the user 102. The camera 104 is shown positioned over a display device 1514 in the room, however, for use of the HMD 900, the camera 104 is placed in any location that can capture images of the HMD 900. As such, the user 102 is shown turned at about 90 degrees from the camera 104 and the display device 1514, as content rendered in the HMD 900 is dependent on the direction that the HMD 900 is positioned, from the perspective of the camera 104. Of course, during use of the HMD 900, the user 102 will be moving about, turning his/her head, looking in various directions, as is needed to take advantage of the dynamic virtual scenes rendered by the HMD 900.

Figure 16:
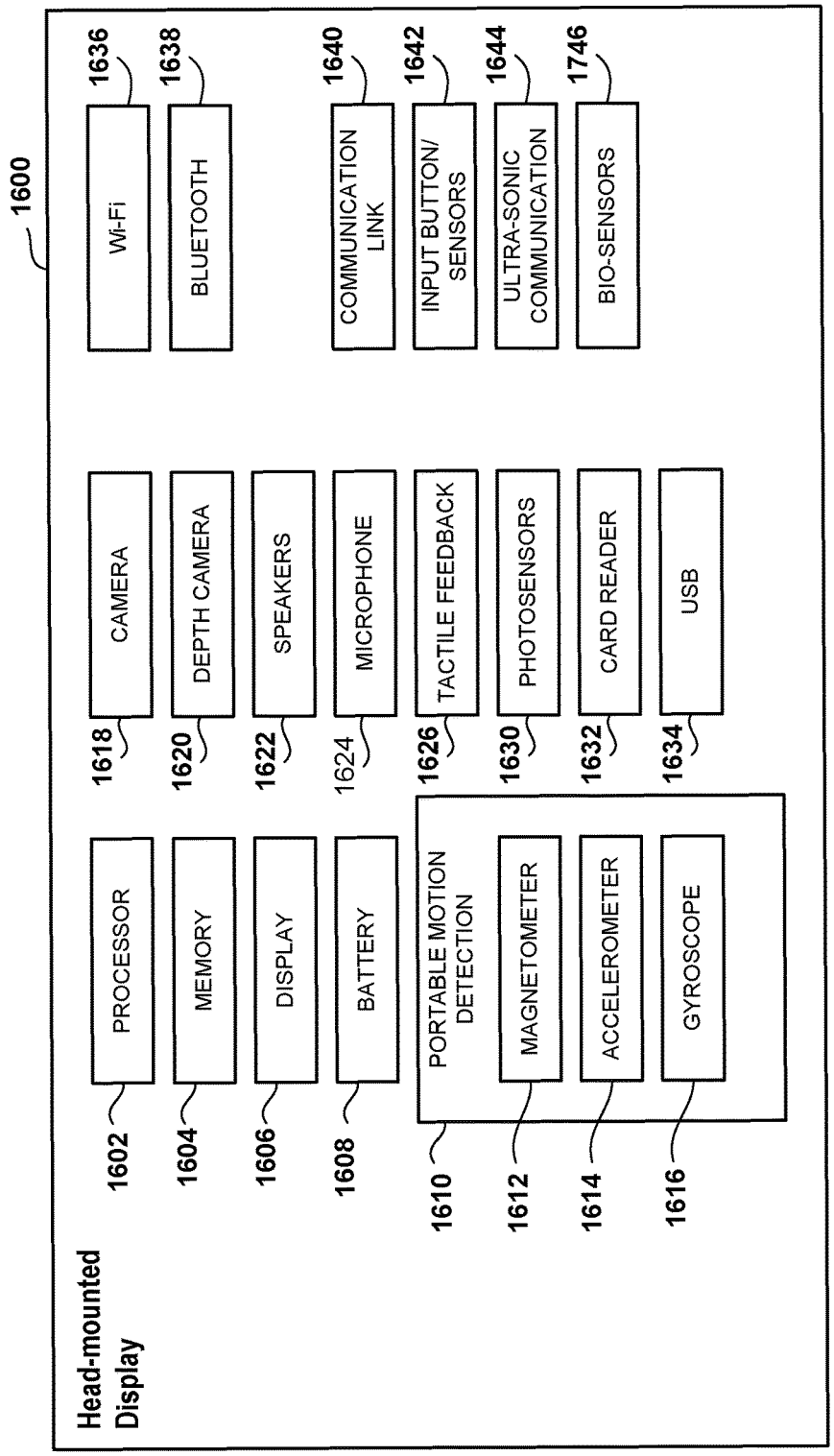
FIG. 16 is a diagram of an embodiment of an HMD.

With reference to FIG. 16, a diagram is shown illustrating example components of an HMD 1600, in accordance with an embodiment described in the present disclosure. The HMD 1600 is an example of the HMD 110 shown in FIG. 1A, or the HMD 132 of FIG. 1B, or the HMD 152 of FIG. 1C. It should be understood that more or less components can be included or excluded from the HMD 1600, depending on the configuration and functions enabled. The HMD 1600 includes a processor 1602 for executing program instructions described herein as being executed by the processor of the HMD 1600. A memory device 1604 of the HMD 1600 is provided for storage purposes, and in one embodiment, includes both volatile and non-volatile memory. A display 1606 is included within the HMD 1600 to provide a visual interface that the user 102 views.

The display 1606 is defined by one single display screen, or in the form of a separate display screen for each eye of the user 102. When two display screens are provided, it is possible to provide left-eye and right-eye video content separately. Separate presentation of video content to each eye, for example, provides for better immersive control of 3D content. As described herein, in one embodiment, the second screen is provided with second screen content of the HMD 1600 by using the output for one eye, and then formatting the content for display in a two-dimensional (2D) format. The one eye, in one embodiment, is the left-eye video feed, but in other embodiments is the right-eye video feed.

A battery 1608 is provided as a power source for the HMD 1600. In other embodiments, the power source includes an outlet connection to power. In other embodiments, an outlet connection to power and the battery 1608 are provided. A motion detection module 1610 includes any of various kinds of motion sensitive hardware, such as a magnetometer 1612, an accelerometer 1614, and a gyroscope 1616.

An accelerometer 1614 is a device for measuring acceleration and gravity induced reaction forces. Single and multiple axis (e.g., six-axis) models are able to detect magnitude and direction of the acceleration in different directions. The accelerometer 1614 is used to sense inclination, vibration, and shock. In one embodiment, three accelerometers are used to provide the direction of gravity, which gives an absolute reference for two angles (world-space pitch and world-space roll).

A magnetometer 1612 measures the strength and direction of the magnetic field in the vicinity of the HMD 1600. In one embodiment, three magnetometers are used within the HMD 1600, ensuring an absolute reference for the world-space yaw angle. In one embodiment, the magnetometer 1612 is designed to span the earth magnetic field, which is ±80 microtesla. Magnetometers are affected by metal, and provide a yaw measurement that is monotonic with actual yaw. The magnetic field is warped due to metal in the environment, which causes a warp in the yaw measurement. If necessary, this warp is calibrated using information from other sensors such as the gyroscope or the camera. In one embodiment, the accelerometer 1614 is used together with magnetometer 1612 to obtain the inclination and azimuth of the HMD 1600.

A gyroscope 1616 is a device for measuring or maintaining orientation, based on the principles of angular momentum. In one embodiment, three gyroscopes provide information about movement across the respective axis (x, y and z) based on inertial sensing. The gyroscopes help in detecting fast rotations. However, the gyroscopes drift overtime without the existence of an absolute reference. To reduce the drift, the gyroscopes are reset periodically, which can be done using other available information, such as positional/orientation determination based on visual tracking of an object, accelerometer, magnetometer, etc.

A camera 1618 is provided for capturing images and image streams of the real-world environment. In one embodiment, more than one camera (optionally) is included in the HMD 1600, including a camera that is rear-facing (directed away from the user when the user is viewing the display of the HMD 1600), and a camera that is front-facing (directed towards the user when the user is viewing the display of the HMD 1600). Additionally, in an embodiment, a depth camera 1620 is included in the HMD 1600 for sensing depth information of objects in the real-world environment.

The HMD 1600 includes speakers 1622 for providing audio output. Also, in one embodiment, a microphone 1624 is included for capturing audio from the real-world environment, including sounds from the ambient environment, speech made by the user, etc. In an embodiment, the HMD 1600 includes tactile feedback module 1626 for providing tactile feedback to the user 102. In one embodiment, the tactile feedback module 1626 is capable of causing movement and/or vibration of the HMD 1600 so as to provide tactile feedback to the user.

Photosensors 1630 are provided to detect one or more of the beams. A card reader 1632 is provided to enable the HMD 1600 to read and write information to and from a memory card. A USB interface 1634 is included as one example of an interface for enabling connection of peripheral devices, or connection to other devices, such as other portable devices, computers, game consoles, etc. In various embodiments of the HMD 1600, any of various kinds of interfaces may be included to enable greater connectivity of the HMD 1600.

In an embodiment, a Wi-Fi module 1636 is included for enabling connection to the computer network via wireless networking technologies. Also, in one embodiment, the HMD 1600 includes a Bluetooth module 1638 for enabling wireless connection to other devices. A communications link 1640 is included for connection to other devices. In one embodiment, the communications link 1640 utilizes infrared transmission for wireless communication. In other embodiments, the communications link 1640 utilizes any of various wireless or wired transmission protocols for communication with other devices.

Input buttons/sensors 1642 are included to provide an input interface for the user. Any of various kinds of input interfaces may be included, such as buttons, gestures, touchpad, joystick, trackball, etc. In one embodiment, an ultrasonic communication module 1644 is included in HMD 1600 for facilitating communication with other devices via ultra-sonic technologies.

In an embodiment, bio-sensors 1646 are included to enable detection of physiological data from the user 102. In one embodiment, the bio-sensors 1646 include one or more dry electrodes for detecting bio-electric signals of the user through the user's skin, voice detection, eye retina detection to identify users/profiles, etc.

The foregoing components of HMD 1600 have been described as merely exemplary components that may be included in HMD 1600. In various embodiments described in the present disclosure, the HMD 1600 may or may not include some of the various aforementioned components. Embodiments of the HMD 1600 may additionally include other components not presently described, but known in the art, for purposes of facilitating aspects of the present invention as herein described.

In one embodiment, the HMD 1600 includes light emitting diodes, which are used in addition to the photosensors 1630 to determine a position and/or orientation of the HMD 1600. For example, the LEDs and a camera located within the environment in which the HMD 1600 is located are used to confirm or deny a position and/or orientation that is determined using the photosensors 1630 and the methods described herein.

It will be appreciated by those skilled in the art that in various embodiments described in the present disclosure, the aforementioned handheld device is utilized in conjunction with an interactive application displayed on a display to provide various interactive functions. The exemplary embodiments described herein are provided by way of example only, and not by way of limitation.

In one embodiment, clients and/or client devices, as referred to herein, may include HMDs, terminals, personal computers, game consoles, tablet computers, telephones, set-top boxes, kiosks, wireless devices, digital pads, stand-alone devices, handheld game playing devices, and/or the like. Typically, clients are configured to receive encoded video streams, decode the video streams, and present the resulting video to a user, e.g., a player of a game. The processes of receiving encoded video streams and/or decoding the video streams typically includes storing individual video frames in a receive buffer of the client. The video streams may be presented to the user 102 on a display integral to client or on a separate device such as a monitor or television.

Clients are optionally configured to support more than one game player. For example, a game console may be configured to support two, three, four or more simultaneous players (e.g., P1, P2, . . . Pn). Each of these players receives or shares a video stream, or a single video stream may include regions of a frame generated specifically for each player, e.g., generated based on each player's point of view. Any number of clients are local (e.g., co-located) or are geographically dispersed. The number of clients included in a game system vary widely from one or two to thousands, tens of thousands, or more. As used herein, the term "game player" is used to refer to a person that plays a game and the term "game playing device" is used to refer to a device used to play a game. In some embodiments, the game playing device may refer to a plurality of computing devices that cooperate to deliver a game experience to the user.

For example, a game console and an HMD cooperate with a video server system to deliver a game viewed through the HMD. In one embodiment, the game console receives the video stream from the video server system and the game console forwards the video stream, or updates to the video stream, to the HMD and/or television for rendering.

Still further, an HMD is used for viewing and/or interacting with any type of content produced or used, such video game content, movie content, video clip content, web content, advertisement content, contest content, gamboling game content, conference call/meeting content, social media content (e.g., posting, messages, media streams, friend events and/or game play), video portions and/or audio content, and content made for consumption from sources over the internet via browsers and applications and any type of streaming content. Of course, the foregoing listing of content is not limiting, as any type of content can be rendered so long as it can be viewed in the HMD or rendered to a screen or screen of the HMD.

In one embodiment, clients further include systems for modifying received video. For example, a client performs further rendering, to overlay one video image on another video image, to crop a video image, and/or the like. As another example, clients receive various types of video frames, such as I-frames, P-frames and B-frames, and to process these frames into images for display to a user. In some embodiments, a member of clients is configured to perform further rendering, shading, conversion to 3-D, conversion to 2D, distortion removal, sizing, or like operations on the video stream. A member of clients is optionally configured to receive more than one audio or video stream.

Input devices of clients includes, for example, a one-hand game controller, a two-hand game controller, a gesture recognition system, a gaze recognition system, a voice recognition system, a keyboard, a joystick, a pointing device, a force feedback device, a motion and/or location sensing device, a mouse, a touch screen, a neural interface, a camera, input devices yet to be developed, and/or the like.

In some embodiments, a video source includes rendering logic, e.g., hardware, firmware, and/or software stored on a computer readable medium such as storage. This rendering logic is configured to create video frames of the video stream based on the game state. All or part of the rendering logic is optionally disposed within one or more graphics processing unit (GPU). Rendering logic typically includes processing stages configured for determining the three-dimensional spatial relationships between objects and/or for applying appropriate textures, etc., based on the game state and viewpoint. The rendering logic produces raw video that is encoded. For example, the raw video is encoded according to an Adobe Flash® standard, HTML-5, .wav, H.264, H.263, On2, VP6, VC-1, WMA, Huffyuv, Lagarith, MPG-x, Xvid, FFmpeg, x264, VP6-8, real video, mp3, or the like. The encoding process produces a video stream that is optionally packaged for delivery to a decoder on a device. The video stream is characterized by a frame size and a frame rate. Typical frame sizes include 800×600, 1280×720 (e.g., 720p), 1024×768, 1080p, although any other frame sizes may be used. The frame rate is the number of video frames per second. In one embodiment, a video stream includes different types of video frames. For example, the H.264 standard includes a "P" frame and a "I" frame. I-frames include information to refresh all macro blocks/pixels on a display device, while P-frames include information to refresh a subset thereof. P-frames are typically smaller in data size than are I-frames. As used herein the term "frame size" is meant to refer to a number of pixels within a frame. The term "frame data size" is used to refer to a number of bytes required to store the frame.

In some embodiments, the client is a general purpose computer, a special purpose computer, a game console, a personal computer, a laptop computer, a tablet computer, a mobile computing device, a portable gaming device, a cellular phone, a set-top box, a streaming media interface/device, a smart television or networked display, or any other computing device capable of being configured to fulfill the functionality of a client as defined herein. In one embodiment, a cloud gaming server is configured to detect the type of client device which is being utilized by the user, and provide a cloud-gaming experience appropriate to the user's client device. For example, image settings, audio settings and other types of settings may be optimized for the user's client device.

Figure 17:
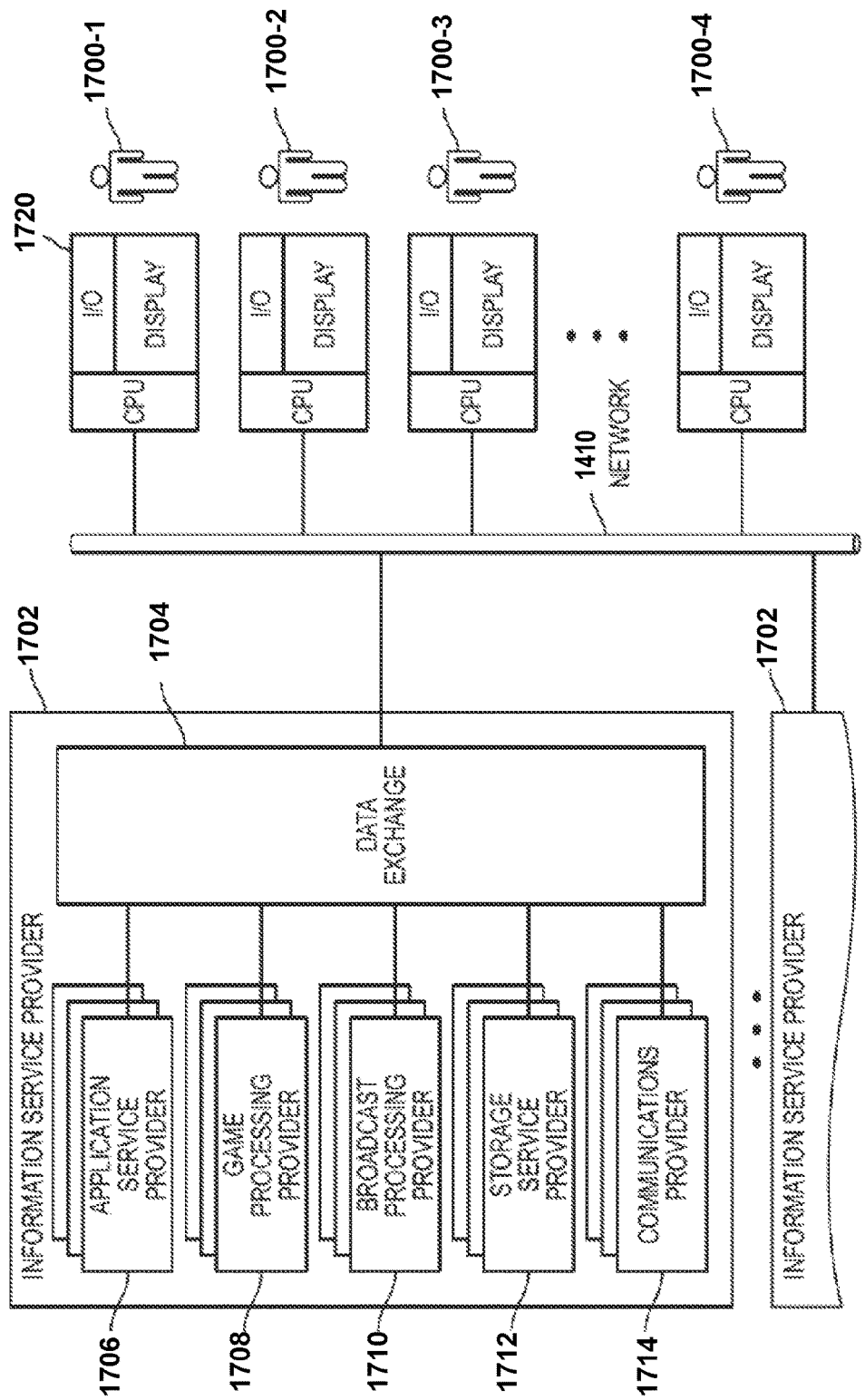
FIG. 17 illustrates an embodiment of an Information Service Provider architecture.

FIG. 17 illustrates an embodiment of an Information Service Provider architecture.

Information Service Providers (ISP) 1702 delivers a multitude of information services to users 1700-1, 1700-2, 1700-3, 1700-4, etc., geographically dispersed and connected via the computer network 1310. It should be noted that instead of any of the users 1700-1, or 1700-2, or 1700-3, and 1700-4, the user 102 receives the multitude of information services. In one embodiment, an ISP delivers one type of service, such as stock price updates, or a variety of services such as broadcast media, news, sports, gaming, etc. Additionally, the services offered by each ISP are dynamic, that is, services can be added or taken away at any point in time. Thus, the ISP providing a particular type of service to a particular individual can change over time. For example, a user is served by an ISP in near proximity to the user while the user is in her home town, and the user is served by a different ISP when the user travels to a different city. The home-town ISP will transfer the required information and data to the new ISP, such that the user information "follows" the user to the new city making the data closer to the user and easier to access. In another embodiment, a master-server relationship is established between a master ISP, which manages the information for the user, and a server ISP that interfaces directly with the user under control from the master ISP. In another embodiment, the data is transferred from one ISP to another ISP as the client moves around the world to make the ISP in better position to service the user be the one that delivers these services.

ISP 1702 includes Application Service Provider (ASP) 1706, which provides computer-based services to customers over the computer network 1310. Software offered using an ASP model is also sometimes called on-demand software or software as a service (SaaS). A simple form of providing access to a particular application program (such as customer relationship management) is by using a standard protocol such as HTTP. The application software resides on the vendor's system and is accessed by users through a web browser using HTML, by special purpose client software provided by the vendor, or other remote interface such as a thin client.

Services delivered over a wide geographical area often use cloud computing. Cloud computing is a style of computing in which dynamically scalable and often virtualized resources are provided as a service over the computer network 1310. Users do not need to be an expert in the technology infrastructure in the "cloud" that supports them. In one embodiment, cloud computing are divided in different services, such as Infrastructure as a Service (IaaS), Platform as a Service (PaaS), and Software as a Service (SaaS). Cloud computing services often provide common business applications online that are accessed from a web browser, while the software and data are stored on the servers. The term cloud is used as a metaphor for the Internet (e.g., using servers, storage and logic), based on how the Internet is depicted in computer network diagrams and is an abstraction for the complex infrastructure it conceals.

Further, ISP 1702 includes a Game Processing Server (GPS) 1708 which is used by game clients to play single and multiplayer video games. Most video games played over the Internet operate via a connection to a game server. Typically, games use a dedicated server application that collects data from players and distributes it to other players. This is more efficient and effective than a peer-to-peer arrangement, but it requires a separate server to host the server application. In another embodiment, the GPS establishes communication between the players and their respective game-playing devices exchange information without relying on the centralized GPS.

Dedicated GPSs are servers which run independently of the client. Such servers are usually run on dedicated hardware located in data centers, providing more bandwidth and dedicated processing power. Dedicated servers are the preferred method of hosting game servers for most PC-based multiplayer games. Massively multiplayer online games run on dedicated servers usually hosted by the software company that owns the game title, allowing them to control and update content.

Broadcast Processing Server (BPS) 1710 distributes audio or video signals to an audience. Broadcasting to a very narrow range of audience is sometimes called narrowcasting. The final leg of broadcast distribution is how the signal gets to the listener or viewer, and it may come over the air as with a radio station or TV station to an antenna and receiver, or may come through cable TV or cable radio (or "wireless cable") via the station or directly from a network. The Internet may also bring either radio or TV to the recipient, especially with multicasting allowing the signal and bandwidth to be shared. Historically, broadcasts have been delimited by a geographic region, such as national broadcasts or regional broadcast. However, with the proliferation of fast internet, broadcasts are not defined by geographies as the content can reach almost any country in the world.

Storage Service Provider (SSP) 1712 provides computer storage space and related management services. SSPs also offer periodic backup and archiving. By offering storage as a service, users can order more storage as required. Another major advantage is that SSPs include backup services and users will not lose all their data if their computers' hard drives fail. Further, in an embodiment, a plurality of SSPs have total or partial copies of the user data, allowing users to access data in an efficient way independently of where the user is located or the device being used to access the data. For example, a user can access personal files in the home computer, as well as in a mobile phone while the user is on the move.

Communications Provider 1714 provides connectivity to the users. One kind of Communications Provider is an Internet Service Provider (ISP) which offers access to the Internet. The ISP connects its customers using a data transmission technology appropriate for delivering Internet Protocol datagrams, such as dial-up, DSL, cable modem, fiber, wireless or dedicated high-speed interconnects. The Communications Provider can also provide messaging services, such as e-mail, instant messaging, and SMS texting. Another type of Communications Provider is the Network Service provider (NSP) which sells bandwidth or network access by providing direct backbone access to the Internet. Network service providers, in one embodiment, include telecommunications companies, data carriers, wireless communications providers, Internet service providers, cable television operators offering high-speed Internet access, etc.

Data Exchange 1704 interconnects the several modules inside ISP 1702 and connects these modules to users 1700 via the computer network 1310. Data Exchange 1704 covers a small area where all the modules of ISP 1702 are in close proximity, or covers a large geographic area when the different modules are geographically dispersed. For example, Data Exchange 1788 includes a fast Gigabit Ethernet (or faster) within a cabinet of a data center, or an intercontinental virtual area network (VLAN).

Users 1700 access the remote services with client device 1720, which includes at least a CPU, a display and an input/output (I/O) device. The client device can be a personal computer (PC), a mobile phone, a netbook, tablet, gaming system, a personal digital assistant (PDA), etc. In one embodiment, ISP 1702 recognizes the type of device used by the client and adjusts the communication method employed. In other cases, client devices use a standard communications method, such as html, to access ISP 1702.

It should be noted that the above-described embodiments are applicable to interactive content, e.g., virtual reality, augmented reality, etc., which is generated by execution of a program application, e.g., a computer program to communicate via the Internet with other people, the game code, a computer program for displaying a virtual reality scene, a computer program for displaying an augmented reality scene, etc. In some embodiments, the video game is an example of virtual reality content or of augmented reality content.

Embodiments described in the present disclosure may be practiced with various computer system configurations including hand-held devices, microprocessor systems, microprocessor-based or programmable consumer electronics, minicomputers, mainframe computers and the like. The embodiments described in the present disclosure can also be practiced in distributed computing environments where tasks are performed by remote processing devices that are linked through a wire-based or wireless network.

With the above embodiments in mind, it should be understood that the embodiments described in the present disclosure can employ various computer-implemented operations involving data stored in computer systems. These operations are those requiring physical manipulation of physical quantities. Any of the operations described herein that form part of the embodiments described in the present disclosure are useful machine operations. Some embodiments described in the present disclosure also relate to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

Some embodiments described in the present disclosure can also be embodied as computer readable code on a computer readable medium. The computer readable medium is any data storage device that can store data, which can be thereafter be read by a computer system. Examples of the computer readable medium include a hard drive, a NAS, a ROM, a RAM, a CD-ROM, a CD-R, a CD-RW, a magnetic tape, an optical data storage device, a non-optical data storage device, etc. The computer readable medium can include computer readable tangible medium distributed over a network-coupled computer system so that the computer readable code is stored and executed in a distributed fashion.

It should be noted that in some embodiments, any of the embodiments described herein are combined with any of the remaining embodiments.

Moreover, although some of the above-described embodiments are described with respect to a gaming environment, in some embodiments, instead of a game, other environments, e.g., a video conferencing environment, etc., is used.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing embodiments described in the present disclosure have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

The invention claimed is:

1. A method for identifying an obstruction to a trackable field-of-view (FOV) of a tracker, comprising:
    executing interactive content for display of a plurality of images on a head-mounted display, wherein the head-mounted display is configured to be worn by a user, wherein the execution of the interactive content is changed based on changes in a position and orientation of the head-mounted display when tracked by the tracker;
    determining that the trackable FOV is obstructed by a spectator during the execution of the interactive content when the spectator is not visible via the head-mounted display to the user, wherein the obstruction by the spectator reduces a quality factor associated with tracking of the position and orientation used for generating the plurality of images displayed on the head-mounted display; and
    notifying the user that the quality factor has reduced as a result of the obstruction by the spectator, wherein said notifying is provided by a message rendered by the head-mounted display.

2. The method of claim 1, wherein determining that the trackable FOV is obstructed by the spectator comprises determining that the head-mounted display is blocked for a period of time, wherein the block reduces continuous tracking of the position and orientation during the period of time used to achieve a frame rate.

3. The method of claim 1, further comprising determining an identity of the spectator upon determining that the trackable FOV is obstructed by the spectator, wherein determining the identity of the spectator includes detecting, by the tracker, a human face proximate to the head-mounted display.

4. The method of claim 1, wherein the message includes an image notification for display on the head-mounted display to indicate to the user that the trackable FOV is obstructed by the spectator.

5. The method of claim 1, further comprising generating an audio notification for outputting a sound via the head-mounted display indicating that the trackable FOV is obstructed by the spectator.

6. The method of claim 1, wherein the tracker is a camera placed to have a view of the head-mounted display, or a combination of a projector and photosensors, or a camera of the head-mounted display.

7. The method of claim 1, further comprising determining an identity of the spectator upon determining that the trackable FOV is obstructed by the spectator, wherein determining the identity of the spectator comprises controlling a shutter speed of a camera and an aperture diaphragm of the camera to focus on the spectator instead of the head-mounted display.

8. The method of claim 1, wherein the reduction in the quality factor is associated with a drop in presentation quality of the plurality of images as displayed on the head-mounted display.

9. The method of claim 1, further comprising notifying the spectator that the spectator is obstructing the trackable FOV.

10. A method for identifying a spectator to a user during interaction with interactive content on a head-mounted display, comprising:
    determining that the spectator is within a trackable field-of-view (FOV) of a tracker, wherein said determining that the spectator is within the trackable FOV is performed when interactive content is executed to display the interactive content on the head-mounted display, wherein the head-mounted display is configured to be worn by the user during the execution of the interactive content;
    determining that the spectator is identifiable upon determining that the spectator is within the trackable FOV;
    determining that the spectator is obstructing the trackable FOV when the spectator is not visible via the head-mounted display to the user; and
    notifying the user that the spectator is obstructing the trackable FOV in response to determining that the spectator is obstructing the trackable FOV.

11. The method of claim 10, wherein determining that the spectator is obstructing the trackable FOV comprises determining that the head-mounted display is blocked for a period of time, wherein the block reduces continuous tracking of a position and orientation of the head-mounted display during the period of time used to achieve a frame rate.

12. The method of claim 10, wherein notifying the user includes generating an image notification for display on the head-mounted display to indicate to the user that the trackable FOV is obstructed by the spectator.

13. The method of claim 10, wherein notifying the user includes generating an audio notification for outputting a sound via the head-mounted display indicating that the trackable FOV is obstructed by the spectator.

14. The method of claim 10, wherein the tracker is a camera placed to have a view of the head-mounted display, or is a combination of a projector and photosensors, or is a camera of the head-mounted display.

15. The method of claim 10, further comprising identifying the spectator upon determining that the spectator is obstructing the trackable FOV.

16. A system for identifying an obstruction to a trackable field-of-view (FOV) of a tracker, comprising:
    a head-mounted display configured to be worn by a user to display interactive content; and
    a processor coupled to the head-mounted display, wherein the processor is configured to:
        execute the interactive content for display of a plurality of images on the head-mounted display, wherein the execution of the interactive content is changed based on changes in a position and orientation of the head-mounted display when tracked by the tracker;
        determine that the trackable FOV is obstructed by a spectator during the execution of the interactive content when the spectator is not visible via the head-mounted display to the user, wherein the obstruction by the spectator reduces a quality factor associated with a determination of the position and orientation used to generate the plurality of images displayed on the head-mounted display;
        identify the spectator upon determining that the trackable FOV is obstructed by the spectator; and
        generate a notification to be output via the head-mounted display that the quality factor is reduced as a result of the obstruction by the spectator, wherein the notification is provided by a message rendered by the head-mounted display.

17. The system of claim 16, wherein to determine that the trackable FOV is obstructed by the spectator, the processor is configured to determine that the head-mounted display is blocked for a period of time, wherein the block of the head-mounted display affects continuous tracking of the position and orientation during the period of time used to achieve a frame rate.

18. The system of claim 16, wherein to identify the spectator, the processor is configured to change a focus of the tracker to the spectator from a focus on the head-mounted display.

19. The system of claim 16, wherein the message includes an image notification for display on the head-mounted display to indicate to the user that the trackable FOV is obstructed by the spectator.

20. The system of claim 16, wherein to generate the notification, the processor is configured to generate an audio notification for outputting a sound via the head-mounted display to indicate to the user that the trackable FOV is obstructed by the spectator.

21. The system of claim 16, wherein the tracker is a camera placed to have a view of the head-mounted display, or a combination of a projector and photosensors, or a camera of the head-mounted display.

22. The system of claim 16, wherein to identify the spectator, the processor is configured to control a shutter speed of a camera and an aperture diaphragm of the camera to focus on the spectator instead of the head-mounted display.

23. The method of claim 1, wherein when the quality factor is reduced, one of the plurality of images is not displayed.

24. The method of claim 1, wherein the reduction in the quality factor includes a decrease in a frame rate at which the plurality of images are displayed on the head-mounted display or a reduction in speed of generation of one of more game states based on the position and orientation.

* * * * *